US010982194B2

(12) United States Patent
Cerullo et al.

(10) Patent No.: US 10,982,194 B2
(45) Date of Patent: Apr. 20, 2021

(54) NON-GENETIC MODIFICATION OF ENVELOPED VIRUSES

(71) Applicant: VALO THERAPEUTICS OY, Helsinki (FI)

(72) Inventors: Vincenzo Cerullo, Helsinki (FI); Cristian Capasso, Helsinki (FI); Erkko Ylosmaki, Sipoo (FI)

(73) Assignee: VALO THERAPEUTICS OY, Helsinki (FI)

( * ) Notice: Subject to any disclaimer, the term of this patent is extended or adjusted under 35 U.S.C. 154(b) by 0 days.

(21) Appl. No.: 16/337,220

(22) PCT Filed: Sep. 6, 2017

(86) PCT No.: PCT/EP2017/072366
§ 371 (c)(1),
(2) Date: Mar. 27, 2019

(87) PCT Pub. No.: WO2018/059896
PCT Pub. Date: Apr. 5, 2018

(65) Prior Publication Data
US 2020/0010811 A1    Jan. 9, 2020

(30) Foreign Application Priority Data

Sep. 27, 2016    (GB) .................................... 1616365

(51) Int. Cl.
| A01N 63/00 | (2020.01) |
| C12N 7/00 | (2006.01) |
| C12N 7/01 | (2006.01) |
| A01N 63/02 | (2006.01) |
| A01N 65/00 | (2009.01) |
| A61K 39/00 | (2006.01) |

(52) U.S. Cl.
CPC ............ *C12N 7/00* (2013.01); *A61K 39/0011* (2013.01); *A61K 2039/5256* (2013.01); *C12N 2710/24122* (2013.01); *C12N 2710/24132* (2013.01)

(58) Field of Classification Search
CPC .. A61K 2300/00; A61K 38/21; A61K 35/768; A61K 38/191; A61K 38/2013
See application file for complete search history.

(56) References Cited

U.S. PATENT DOCUMENTS

| 7,273,752 B2 | 9/2007 | Chen et al. |
| 2006/0002893 A1 | 1/2006 | Vigne et al. |
| 2011/0059135 A1 | 3/2011 | Kovesdi et al. |
| 2013/0243731 A1 | 9/2013 | Dias et al. |
| 2014/0140962 A1 | 5/2014 | Carrico et al. |
| 2017/0080069 A1 | 3/2017 | Cerullo et al. |

FOREIGN PATENT DOCUMENTS

| ES | 2335077 A1 | 3/2010 |
| WO | 2003/063770 A2 | 8/2003 |
| WO | 2004/000220 A2 | 12/2003 |
| WO | 2005/060541 A2 | 7/2005 |
| WO | 2015/027163 A1 | 2/2015 |
| WO | 2015/177098 A2 | 11/2015 |

OTHER PUBLICATIONS

Patel et al., "Influenza virus-like particles engineered by protein transfer with tumor-associated antigens induces protective antitumor immunity", Biotechnol Bioen, 2015, 112(6):1102-1110.*
Patel et al., "Influenza virus-like particles engineered by protein transfer with tumor-associated antigens induces protective antitumor immunity", Biotechnology Bioengineering, 2015, 112(6):1102-1110.*
Capasso et al., "Oncolytic adenoviruses coated with MHC-I tumor epitopes increase the antitumor immunity and efficacy against melanoma", Oncoimmunology, 2016, 5(4):1-11.*
International Search Report and Written Opinion for PCT/EP2017/072366.
Capasso, C., et al., Oncolytic adenoviruses coated with MHC-I tumor epitopes increase the antitumor immunity and efficacy against melanoma; Oncoimmunology, 2016, vol. 5, No. 4, e1105429.
Heider, S., et al., Biomedical applications of glycosylphosphatidylinositolanchored proteins; Journal of Lipid Research vol. 57, 2016; pp. 1778-1788.
Patel, J., et al., Influenza virus-like particles engineered by protein transfer with tumor-associated antigens induces protective antitumor immunity; Biotechnol Bioeng. Jun. 2015; 112(6): 1102-1110.
Metzner, C., et al., Association of glycosylphosphatidylinositol-anchored protein with retroviral particles; The FASEB Journal; vol. 22 pp. 2734-2739 Aug. 2008.
Capasso, C., et al., Beyond Gene Delivery: Strategies to Engineer the Surfaces of Viral Vectors; Biomedicines 2013, 1, 3-16.
Rehman, H., et al., Into the clinic: Talimogene laherparepvec (T-VEC), a first-in-class intratumoral oncolytic viral therapy; Journal for ImmunoTherapy of Cancer (2016) 4: 53; pp. 1-8.
Hastie, E., et al., Vesicular stomatitis virus as a flexible platform for oncolytic virotherapy against cancer; Journal of General Virology (2012), 93, 2529-2545.
Aitken, A., et al., Taking a Stab at Cancer; Oncolytic Virus-Mediated Anti-Cancer Vaccination Strategies; Biomedicines 2017, 5, 3; pp. 1-18.
Ashkenazi, A., et al., Sphingopeptides: dihydrosphingosine-based fusion inhibitors against wild-type and enfuvirtide-resistant HIV-1; The FASEB Journal, vol. 26, 2012; pp. 4628-4636.
Mohan, K.V.K., et al., Antiviral activity of selected antimicrobial peptides against vaccinia virus, Antiviral Research, vol. 86, 2010, pp. 306-311.

(Continued)

*Primary Examiner* — Barry A Chestnut
(74) *Attorney, Agent, or Firm* — King & Schickli, PLLC

(57) ABSTRACT

The invention concerns a modified enveloped virus wherein said virus has at least one anti-tumor, tumor-specific peptide non-genetically attached to or inserted in/through the viral envelope; a pharmaceutical composition comprising same; and a method of treating cancer using same.

23 Claims, 15 Drawing Sheets

Specification includes a Sequence Listing.

(56) References Cited

OTHER PUBLICATIONS

Li, C., et al., A Cholesterol Tag at the N Terminus of the Relatively Broad-Spectrum Fusion Inhibitory Peptide Targets an Earlier Stage of Fusion Glycoprotein Activation and Increases the Peptide's Antiviral Potency In Vivo; Journal of Virology, vol. 87, No. 16; Aug. 2013; pp. 9223-9232.

Galdiero, S., et al., Peptides containing membrane-interacting motifs inhibit herpes simplex virus type 1 infectivity; Peptides 29 (2008); pp. 1461-1471.

UK Intellectual Property Office International Search Report dated Jun. 27, 2017.

Cerullo, et al., Toll-like Receptor 9 Triggers an Innate Immune Response to Helper-dependent Adenoviral Vectors, Am. Soc. of Gene Therapy, Molecular Therapy, vol. 15 No. 2, Feb. 2007, 378-385.

Cerullo, et al., Oncolytic Adenovirus Coding for Granulocyte Macrophage Colony-Stimulating Factor Induces Antitumoral Immunity in Cancer Patients, Cancer Res; 70(11) Jun. 1, 2010, 4297-4309.

Cerullo, et al., An Oncolytic Adenovirus Enhanced for Toll-like Receptor 9 Stimulation Increases Antitumor Immune Responses and Tumor Clearance, Molecular Therapy, vol. 20 No. 11, 2076-2086, Nov. 2012.

Croyle, et al., Development of a Rapid Method for the PEGylation of Adenoviruses with Enhanced Transduction and Improved Stability under Harsh Storage Conditions, Human Gene Therapy 11:1713-1722 (Aug. 10, 2000).

Deng, et al., Assembly of MHC Class I Molecules with Biosynthesized Endoplasmic Reticulum-Targeted Peptides is Inefficient in Insect Cells and Can be Enhanced by Protease Inhibitors, J. Immunol. 1998; 161:1677-1685.

Degli-Esposti, et al., Close Encounters of Different Kinds:Dendritic Cells and Nk Cells Take Centre Stage, Nature Reviews, Feb. 2005 I vol. 5, 112-124.

Dell, et al., Sample Size Determination, ILAR Journal, vol. 43, No. 4, 2002, pp. 207-213.

E. Ramakrishna, et al., Antitumoral Immune Response by Recruitment and Expansion of Dendritic Cells in Tumors Infected with Telomerase-Dependent Oncolytic Viruses, Cancer Res 2009; 69: (4), Feb. 15, 2009, pp. 1448-1458.

Fasbender, et al., Complexes of Adenovirus with Polycationic Polymers and Cationic Lipids Increase the Efficiency of Gene Transfer in Vitro and in Vivo*, J. Biol. Chem. 1997, 272: 6479-6489.

Fortier, et al., The MHC class I peptide repertoire is molded by the transcriptome. J. Experimental. Medicine, vol. 205, No. 3, Mar. 17, 2008 595-610.

Heise, et al., ONYX-015, an E1B gene-attenuated adenovirus, causes tumor-specific cytolysis and antitumoral efficacy that can be augmented by standard chemotherapeutic agents, Nature Medicine, vol. 3, No. 6, Jun. 1997, 639-645.

Heise, et al., An adenovirus E1A mutant that demonstrates potent and selective systemic anti-tumoral efficacy, Nature Medicine, vol. 6, No. 10 Oct. 2000, 1134-1139.

Istrail, et al., Comparative immunopeptidomics of humans and their pathogens, PNAS Sep. 7, 2004, Vo. 101, No. 36 13268-13272.

Lipscomb, et al., Dendritic Cells: Immune Regulators in Health and Disease, Physiol. Rev. 82: 97-130, 2002.

Mocellin, Peptides in Melanoma Therapy, Current Pharmaceutical Design, 2012, 18, 820-831.

Moore, et al., Introduction of Soluble Protein into the Class I Pathway of Antigen Processing and Presentation, Cell, vol. 54, 777-785, Sep. 9, 1988.

Muruve, et al., The inflammasome recognizes cytosolic microbial and host DNA and triggers an innate immune response, Nature, vol. 452, Mar. 6, 2008, 103-108.

Nayak, et al., Progress and prospects: immune responses to viral vectors, Gene Therapy vol. 17 2010, 295-304.

Nowak, et al., Induction of Tumor Cell Apoptosis In Vivo Increases Tumor Antigen Cross-Presentation, Cross-Priming Rather than Cross-Tolerizing Host Tumor-Specific CD8 T Cells, J. Immun. 2003; 170, 4905-4913.

Prestwich, et al., The Case of Oncolytic Viruses Versus the Immune System: Waiting on the Judgment of Solomon, Human Gene Therapy 20, Oct. 2009, 1119-1132.

Seiler, et al., Dendritic Cell Function After Gene Transfer with Adenovirus-calcium Phosphate Co-precipitates, www.moleculartherapy.org vol. 15 No. 2, 386-392, Feb. 2007.

Steinman, et al., Tolerogenic Dendritic Cells, Annu. Rev. Immunol. 2003, 21:685-711.

Stevenson, et al., Incorporation of a laminin-derived peptide (SIKVAV) on polymer-modified adenovirus permits tumor-specific targeting via a6-integrins, Cancer Gene Therapy (2007) 14, 335-345.

Suzuki, et al., MyD88-Dependent Silencing of Transgene Expression During the Innate and Adaptive Immune Response to Helper-Dependent Adenovirus, Human Gene Therapy 21:325-336 (Mar. 2010).

Suzuki, et al., NOD2 Signaling Contributes to the Innate Immune Response Against Helper-Dependent Adenovirus Vectors Independently of MyD88 In Vivo, Human Gene Therapy 22:1071-1082 (Sep. 2011).

Tewalt, et al., Viral Sequestration of Antigen Subverts Cross Presentation to CD8+ T Cells, PLos Pathogens, May 2009 vol. 5, Issue 5, 1-12.

Toyoda, et al., Cationic Polymer and Lipids Enhance Adenovirus-Mediated Gene Transfer to Rabbit Carotid Artery, Stroke, 1998; 29 : 2181-2188.

Trinchieri, et al., Cell-mediated cytotoxicity to SV40-specific tumour-associated antigens, Nature, vol. 261, May 27, 1976 312-314.

Van Der Most, et al., Decoding dangerous death: how cytotoxic chemotherapy invokes inflammation, immunity or nothing at all, Cell Death and Differentiation (2008) 15, 13-20.

Wonganan, et al., PEGylated Adenoviruses: From Mice to Monkeys, Viruses 2010, 2, 468-502.

Wongthida, et al., VSV Oncolytic Virotherapy in the B16 Model Depends Upon Intact MyD88 Signaling, Molecular Therapy vol. 19 No. 1 Jan. 2011 150-158.

Zitvogel, et al., Immunological Aspects of Cancer Chemotherapy, Nature Reviews Immunology vol. 8, Jan. 2008, 59-73.

Edukulla, et al., Antitumoral Immune Response by Recruitment and Expansion of Dendritic Cells in Tumors Infected with Telomerase-Dependent Oncolytic Viruses, Cancer Res 2009; 69: (4). Feb. 15, 2009.

Capasso, et al., Oncolytic Adenovirus Loaded with MHC-I Restricted Peptide as Platform for Oncolytic Vaccine, Molecular Therapy vol. 22, Supplement 1, May 2014.

Wang, et al., Oncolytic adenovirus armed with human papillomavirus E2 gene in combination with radiation demonstrates synergistic enhancements of antitumor efficacy, Cancer Gene Therapy (2011) 18, 825-836.

Cody, et al., Expression of osteoprotegerin from a replicating adenovirus inhibits the progression of prostate cancer bone metastases in a murine model, Laboratory Investigation (2013) 93, 268-278.

Jiang, et al., Corrigendum to "Engineering polypeptide coatings to augment gene transduction and in vivo stability of adenoviruses", Journal of Controlled Release 172 (2013) 1161.

Matthews, Q. L. et al. HIV Antigen Incorporation within Adenovirus Hexon Hypervariable 2 for a Novel HIV Vaccine Approach. PLoS ONE, Jul. 2010, vol. 5, Issue 7, e11815, pp. 1-12.

Nigatu, et al., Evaluation of Cell-Penetrating Peptide/Adenovirus Particles for Transduction of CAR-Negative Cells, Journal of Pharmaceutical Sciences, Jun. 2013, vol. 102, No. 6, pp. 1981-1993.

Ramakrishna, et al., Antitumoral Immune Response by Recruitment and Expansion of Dendritic Cells in Tumors Infected with Telomerase-Dependent Oncolytic Viruses, Cancer Res 2009; 69: (4). Feb. 15, 2009.

Vetter, et al., Adenoviral Vectors Coated with PAMAM Dendrimer Conjugates Allow Car Independent Virus Uptake and Targeting to the EGF Receptor, Mol. Pharmaceutics 2013, 10, 606-618.

(56) References Cited

OTHER PUBLICATIONS

Yang, et al., Polyarginine Induces an Antitumor Immune Response through Binding to Toll-Like Receptor 4, Published in final edited form as: Small. Apr. 9, 2014; 10(7): 1250-1254. doi:10.1002/smll.201302887.

Dias, et al., Targeted Chemotherapy for Head and Neck Cancer with a Chimeric Oncolytic Adenovirus Coding for Bifunctional Suicide Protein FCU1, Clin Cancer Res; 16(9) May 1, 2010.

Overwijk, et al., gp100/pmel 17 is a Murine Tumor Rejection Antigen: Induction of "Self"-reactive, Tumoricidal T Cells Using High-affinity, Altered Peptide Ligand, The Journal of Experimental Medicine • vol. 188, No. 2, Jul. 20, 1998 277-286.

Overwijk, et al., B16 as a Mouse Model for Human Melanoma, Curr Protoc Immunol. May 2001 ; CHAPTER: Unit-20.1.

English Machine Translation of ES 2335077 A1.

Written Opinion and International Search Report for PCT/EP2015/060903 dated Dec. 16, 2015.

Final Office Action dated Apr. 18, 2019 in U.S. Appl. No. 15/312,388, filed Nov. 18, 2016.

Non-Final Office Action dated Sep. 7, 2018 in U.S. Appl. No. 15/312,388, filed Nov. 18, 2016.

Jiang et al., "Engineering polypeptide coatings to augment gene transduction and in vivo stability of adenoviruses," Journal of Controlled Release 166: 75-85 (Year: 2013).

Singh et al., "Designer adenoviruses for nanomedicine and nanodiagnostics," Trends in Biotechnology, vol. 27, No. 4: 220-229 (Year: 2009).

Notice of Allowance for U.S. Appl. No. 15/312,388; dated Jul. 7, 2020.

\* cited by examiner

SUMMARY OF THE DATA:

| VIRUS | PEPTIDE ANCHORING TYPE | ANTI-TUMOUR PEPTIDE | ASSESSMENT OF COMPLEX FORMATION | ASSESSMENT OF COMPLEX FORMATION | ASSESSMENT OF COMPLEX FORMATION | ASSESSMENT OF IMMUNOGENICTY OF THE PEPTIDES | MHCI presentation (of PeptiENV platform) and maturation of DC11+ | PeptiENV infectivity on A549 cells | PeptiENV infectivity on A549,B16-OVA,B16-F10, 4T1.MDMBA cancer cells | PeptiENV PLATFORM *in vivo* immunogenicity | PeptiENV platform *in vivo* anti-tumour effects |
|---|---|---|---|---|---|---|---|---|---|---|---|
| vaccinia virus | Cholesterol N-terminus | SIINFEKL | ELISA | | Apogee | CD11c+ presenting SIINFEKL | CD86 and CD101 | wt. like infectivity | | tested | tested |
| vaccinia virus | GRKKRRQRRRPQ N-terminus | SIINFEKL | ELISA | | Apogee | CD11c+ presenting SIINFEKL | CD86 and CD103 | | wt. like infectivity | tested | tested |
| vaccinia virus | GLWRALWRLLRSLWRLLWRA N-terminus | SIINFEKL | ELISA | | | | | | | | |
| vaccinia virus | AGYLLGKINLKALAALAKKIL C-terminus | SIINFEKL | ELISA | | | | | | | | |
| vaccinia virus | RQIKIWFQNRRMKWKK N-terminus | SIINFEKL | ELISA | | | | | | | | |
| vaccinia virus | KLALKLALKALKAALKLA N-terminus | SIINFEKL | ELISA | | | | | | | | |
| vaccinia virus | RRRRRRRRR N-terminus | SIINFEKL | ELISA | | | | | | | | |
| vaccinia virus | RRRRRRRRR C-terminus | SIINFEKL | ELISA | | | | | | | | |
| vaccinia virus | KETWWETWWTEWSQPKKKRKV C-terminus | SIINFEKL | ELISA | | | | | | | | |
| herpes virus | CPP | SIINFEKL | ELISA | fluorescence correlation spectroscopy | | CD11c+ presenting SIINFEKL | | | | tested | tested |

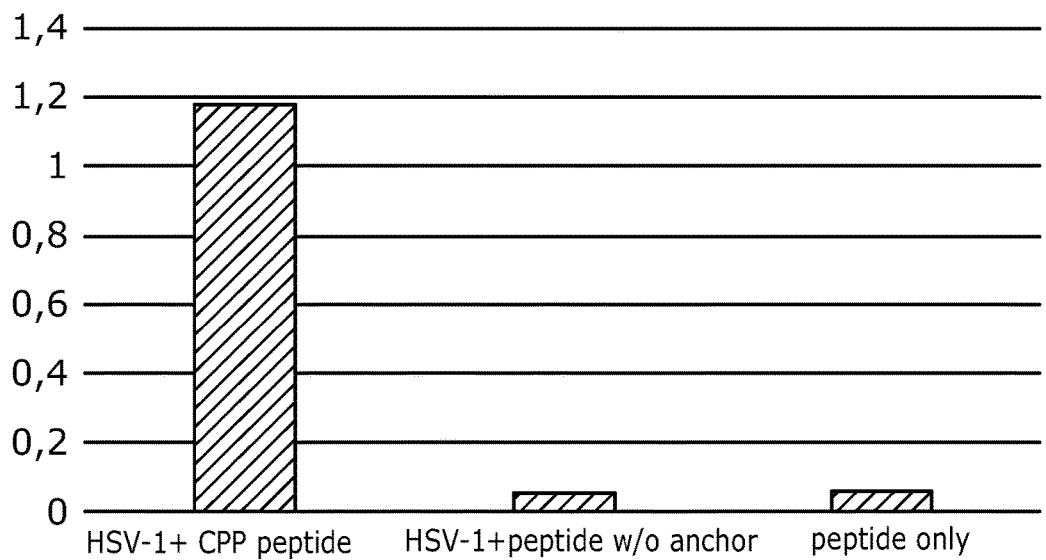
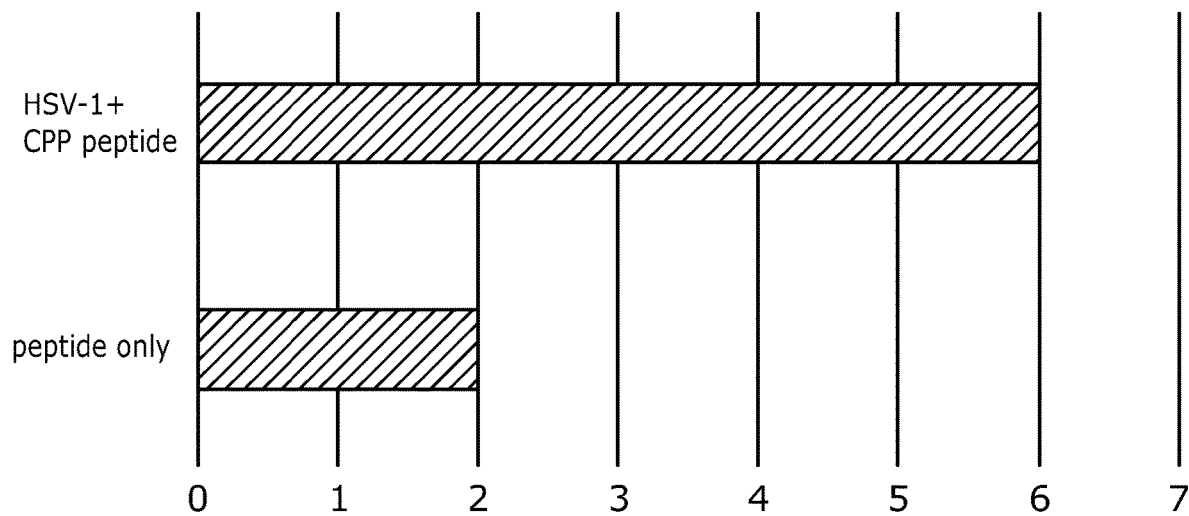
Figure 2

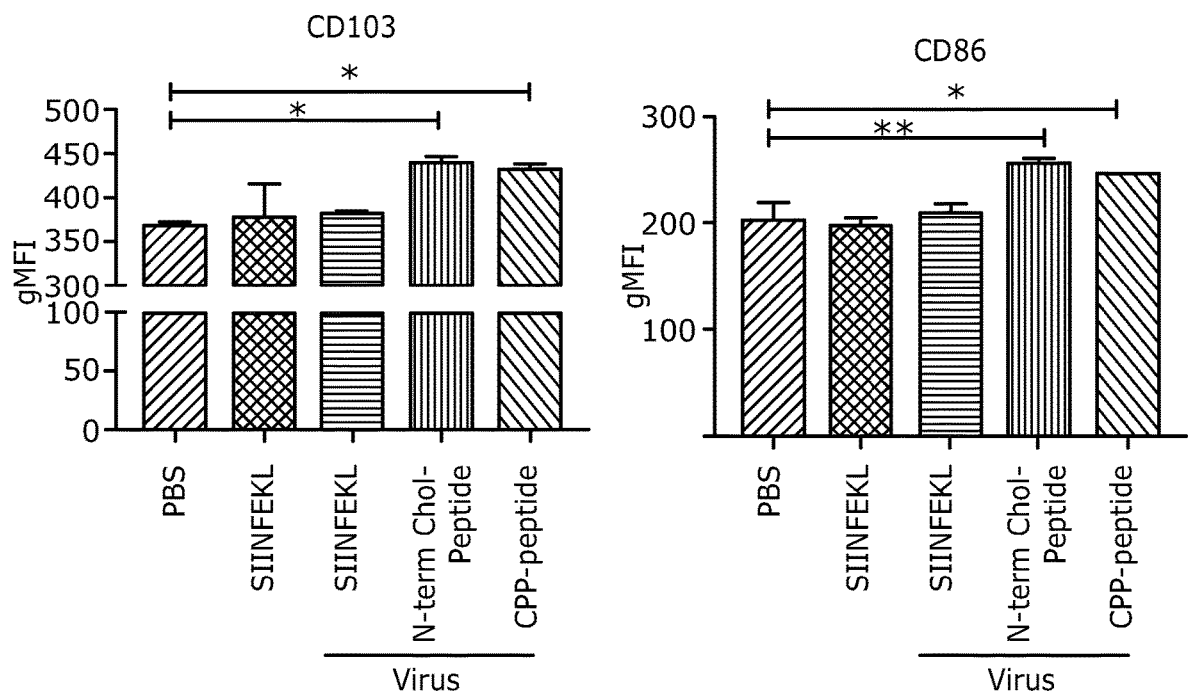
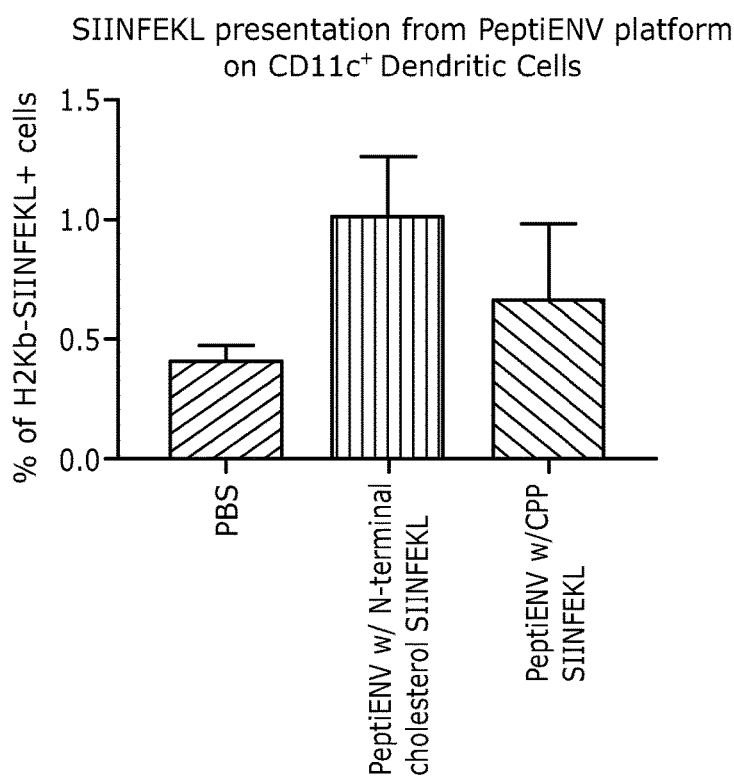
Figure 5

A
cholesterol-CRVRRALISLEQLESIINFEKLTEW (SEQ ID NO:20)

B
GRKKRRQRRRPQRVRRALISLEQLESIINFEKLTEW (SEQ ID NO:8)

NON-GENETIC MODIFICATION OF ENVELOPED VIRUSES

This application is the national stage of international patent application no. PCT/EP2017/072366 filed on Sep. 6, 2017, which in turn claims priority from Great Britain Patent Application No. 1616365.1 filed on Sep. 27, 2016, the disclosures of which are incorporated herein by reference in their entirety.

REFERENCE TO SEQUENCE LISTING SUBMITTED ELECTRONICALLY

A sequence listing electronically submitted with the present application as an ASCII text file named 1776-056SequenceListingrev.txt, created on 8-20-2019 and having a size of 13000 bytes, is incorporated herein by reference in its entirety.

TECHNICAL FIELD

The invention concerns a modified enveloped virus wherein said virus has at least one anti-tumor, tumor-specific peptide non-genetically attached to or inserted in/through the viral envelope; a pharmaceutical composition comprising same; and a method of treating cancer using same.

BACKGROUND

The current paradigm for effective cancer therapeutics is the enhancement of the activity and increase in the amount of tumor infiltrating tumor-specific T-effector cells. These T-effector cells, named CD8+ T cells, specifically cytotoxic T cell lymphocytes (CTLs) are a critical component of the protective immune response against tumors. These tumor-specific CTLs can be found in tumor tissue and there is a clear correlation between the amount of tumor-infiltrated CTLs and patient survival.

A recent approval of antibodies targeting immune checkpoint molecules such as PD-1, PD-L1 and CTLA-4, which function to interrupt the negative feedback systems within the tumor microenvironment to enhance pre-existing anti-tumor immune responses, have been met with tremendous clinical excitement. The use of these immune checkpoint inhibitor antibodies can create durable responses in 10-20% of cancer patients. However, the remaining 80-90% of patients are not responding due to the lack of anti-tumor immune responses or other immune suppressive aspects of the tumor microenvironment. To broaden the patient population responding to checkpoint inhibitor-therapy we have developed an enveloped viral vector platform called PeptiENV for augmenting or generating a broad anti-tumor immunity and to recruit tumor-specific T-effector cells into the tumor microenvironment.

Advantageously, by treating patients with a combination of immunostimulatory PeptiENV viruses and immune checkpoint inhibitor antibodies we expect to increase the amount of responders to the immune checkpoint inhibitor therapies.

This patent application describes a PeptiENV platform, which includes a novel method for coating and inserting immunomodulatory peptides onto a viral envelope which can then be readily cross-presented on antigen presenting cells. Currently there are no methods for non-genetically attaching peptides onto the viral envelope with a view to activating the immune system. WO2005/060541 teaches anti-viral peptides that are inserted into a viral coat for the purposes of disrupting the viral membrane and destroying same.

Some viruses have viral envelopes covering their protective protein capsids. The envelopes are typically derived from portions of the host cell membranes (phospholipids and proteins), but include some viral glycoproteins. They may help viruses avoid the host immune system. Glycoproteins on the surface of the envelope serve to identify and bind to receptor sites on the host's membrane. The viral envelope then fuses with the host's membrane, allowing the capsid and viral genome to enter and infect the host. In addition to entering the host cell via fusion of the viral and host cell membranes, some viruses can alternatively use endocytosis as an entry mechanism.

Essentially, we have found a novel way of boosting anti-tumor immunity at the expense of anti-viral immunity using known therapeutic and clinically approved viruses.

SUMMARY

According to a first aspect, there is provided a modified enveloped virus selected from the group comprising Herpes Simplex Virus 1 (HSV-1), Herpes Simplex Virus 2 (HSV-2), Vaccinia Vesicular stomatitis Indiana virus (VSV), Measles Virus (MeV), Maraba virus and New Castle Disease (NDV) virus wherein said virus has at least one anti-tumor, tumor-specific peptide non-genetically attached to or inserted in/through the viral envelope.

Reference here in to a modified enveloped virus, is to a virus that is modified non-genetically to include said at least one anti-tumor, tumor-specific peptide in its viral envelope. For the avoidance of doubt said virus may or may not include any other genetic modification(s) that make(s) it suitable for its purpose but the attachment of said at least one anti-tumor, tumor-specific peptide to or through the viral envelope is undertaken non-genetically.

Those skilled in the art will realise that some viruses have viral envelopes covering their protective protein capsids. The envelopes are typically derived from portions of the host cell membranes (phospholipids and proteins), but include some viral glycoproteins. They may help viruses avoid the host immune system. Glycoproteins on the surface of the envelope serve to identify and bind to receptor sites on the host's membrane. During infection, the viral envelope fuses with the host's membrane, allowing the capsid and viral genome to enter and infect the host. Peptides attached to or inserted in or taken through the viral envelope can thus be used as antigens to trigger an immune response.

Reference herein to an anti-tumor peptide is to a peptide that can elicit an immune response against a tumor.

Reference herein to a tumor-specific peptide is to a peptide that can elicit an immune response against a particular one or more tumour(s).

In a preferred embodiment said peptide is patient-identified or patient-specific.

As will be apparent to those skilled in the art the exact nature of the peptide can vary having regard to the nature of the tumour to be treated, indeed the specificity of the technology means that different anti-tumor, tumor-specific peptides will be used to treat individuals presenting with different types of cancer and even different anti-tumor, tumor-specific peptides can be used to treat individuals presenting with the same type of cancer.

In yet a further embodiment of the invention said peptide is between 8-50 amino acids long, ideally 15-35 amino acids long. Most ideally said peptide has a length selected form the group comprising: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 amino acids.

Most ideally a plurality of said peptides are attached to or inserted in/through the viral envelope. These peptides may be identical or represent the same antigen with only a minor modification i.e. greater than 90% sequence identity with each other and most ideally greater than 92%, 92%, 93%, 94%, 95%, 96%, 97%, 98%, 99% sequence identity with each other. Alternatively, a number of different anti-tumor, tumor-specific peptides are non-genetically attached to or inserted in/through the viral envelope.

More preferably, said peptide also comprises at least one cleavage site, such as, without limitation, a cathepsin cleavage site or a furin cleavage site. More preferably still, said peptide comprises at least one immunoproteoasome processing site. Examples of these sites and their relative positioning with respect to the structure of the conjugated peptide are shown in FIG. 7. Ideally the one anti-tumor, tumor-specific peptide is positioned between a pair of immunoproteasome processing sites and upstream thereof is at least one cleavage site, ideally a furin cleavage site followed (upstream) by a cathepsin cleavage site.

Advantageously, we have found that these peptides when attached to or inserted in/through selected enveloped viruses (HSV-1 and -2, Vaccinia, VSV, MeV, Maraba virus and NDV) can trigger increased tumor-specific immune responses and drastically enhance anti-tumor efficacy by converting the anti-viral immunity into an anti-tumor immunity.

The elegance of this platform, compared to others, is that by attaching or inserting the patient-identified anti-tumor inducing tumor-specific peptides non-genetically to/in/through the viral envelope we can make clinical use of a medically approved virus. This means one can react very quickly to changes in a patients' tumor antigens that are presented on MHC-I simply by coating the virus with a new set of tumor-specific peptides derived from said patient.

Another important feature of the invention is that the virus chosen for this platform needs to go through rigorous quality control and approval stages only once, thus saving time and money when compared to other platforms where viruses, having genetically introduced modifications, need to go through checking stages every time a new modification or a peptide is introduced, thus making it virtually impossible to use these platforms in personalized medicine.

In a further preferred embodiment of the invention said peptide(s) is/are attached to or inserted in/through said viral envelope using either a cell penetrating peptide or a cholesterol-conjugated peptide (purchased from PepScan or Ontores).

As is known to those skilled in the art, cell penetrating peptides (CPPs) are short peptides that facilitate cellular intake/uptake of various molecular equipment (from nano-size particles to small chemical molecules and large fragments of DNA). This "cargo" is associated with the peptides either through chemical linkage via covalent bonds or through non-covalent interactions. The function of the CPP is to deliver the cargo into cells, a process that commonly occurs through endocytosis.

CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake.

The invention envisages the use of any known CCP when linked with said anti-tumor, tumor-specific peptide.

Without wishing to be bound by an explanation of the mechanism of action, we consider that although CPPs normally deliver their cargo through the lipid bilayer, a peptide consisting of a CPP sequence together with our immunogenic peptide, partially passes through the lipid bilayer while part of it appears to stick, possibly via physical hydrophobic/-philic interactions, on the membrane sufficiently, if not exclusively, for our purposes.

An example of a CPP when conjugated to said peptide is shown in FIG. 7B.

As is also known to those skilled in the art, cholesterol-conjugated peptides are short peptides attached to cholesterol. We have discovered that they can enter the viral envelope and so anchor the conjugated peptide within the viral coat. These peptides can be N- or C-terminally cholesterol conjugated.

Again, without wishing to be bound by an explanation of the mechanism of action, we consider that since cholesterol is a component of a lipid membrane, cholesterol-conjugated peptides find their "normal" location in the membrane. In fact we speculate that the hydroxy group on cholesterol interacts with the polar head groups of the membrane phospholipids and sphingolipids, while the bulky steroid and the hydrocarbon chain are embedded in the membrane, alongside the nonpolar fatty-acid chain of the other lipids.

An example of a cholesterol-conjugated peptide is shown in FIG. 7A.

In a preferred embodiment of the invention the peptide for attaching to or inserting in/through said envelope comprises:

GRKKRRQRRRPQ (SEQ ID NO: 1) CPP sequence in the N- or C-terminus of the said anti-tumor, tumor-specific peptide;

RQIKIWFQNRRMKWKK (SEQ ID NO: 2) CPP sequence in the N- or C-terminus of the said anti-tumor, tumor-specific peptide;

KLALKLALKALKAALKLA (SEQ ID NO: 3) CPP sequence in the N- or C-terminus of the said anti-tumor, tumor-specific peptide;

RRRRRRRRR (SEQ ID NO: 4) CPP sequence in the N- or C-terminus of the said anti-tumor, tumor-specific peptide;

KETWWETWWTEWSQPKKKRKV (SEQ ID NO: 5) CPP sequence in the N- or C-terminus of the said anti-tumor, tumor-specific peptide;

AGYLLGKINLKALAALAKKIL (SEQ ID NO: 6) CPP sequence in the N- or C-terminus of the said anti-tumor, tumor-specific peptide;

AGLWRALWRLLRSLWRLLWRA (SEQ ID NO: 7) CPP sequence in the N- or C-terminus of the said anti-tumor, tumor-specific peptide; or a cholesterol moiety N- or C-terminus of the said anti-tumor, tumor-specific peptide.

In yet a further preferred embodiment of the invention the peptide for attaching to or inserting in/through said envelope comprises one of the following wherein the sequence SIIN-FEKL is simply representative of a MHC-I restricted epitope or peptide:

CPP peptides:

(SEQ ID NO: 8)
GRKKRRQRRRPQRVRRALISLEQLESIINFEKLTEW (SEQ ID NO: 9)
RQIKIWFQNRRMKWKKRWEKISIINFEKLYKLK (SEQ ID NO: 10)
KLALKLALKALKAALKLARWEKISIINFEKLYKLK (SEQ ID NO: 11)
RRRRRRRRRWEKISIINFEKLYKLK (SEQ ID NO: 12)
RWEKISIINFEKLYKLRRRRRRRRR (SEQ ID NO: 13)
RWEKISIINFEKLYKLKETWWETWWTEWSQPKKKRKV (SEQ ID NO: 14)
RWEKISIINFEKLYKLAGYLLGKINLKALAALAKKIL (SEQ ID NO: 15)
AGLWRALWRLLRSLWRLLWRA RWEKISIINFEKLYKLK (SEQ ID NO: 16)
GRKKRRQRRRPQRWEKISIINFEKLYKL (SEQ ID NO: 17)
GRKKRRQRRRPQRWEKISIINFEKL (SEQ ID NO: 18)
GRKKRRQRRRPQRWEKISIINFEKLYKLRWEKISIINFEKL (where RWEKI and YKLRWEKI are immunoproteasome processing sites).

Cholesterol-conjugated peptides:

(SEQ ID NO: 19)
LEQLESIINFEKLTEWRVRRALISC-cholesterol (SEQ ID NO: 20)
cholesterol-CRVRRALISLEQLESIINFEKLTEW (SEQ ID NO: 21)
cholesterol-CSIINFEKL (SEQ ID NO: 22)
cholesterol-CRWEKISIINFEKL
or (SEQ ID NO: 23)
cholesterol-CRWEKISVYDFFVWLYKLRWEKISIINFEKL Accordingly, most preferably said anti-tumor, tumor-specific peptide(s) is/are attached to or inserted in/through said viral envelope using either a cell penetrating peptide or a cholesterol-conjugated peptide.

Typically virus particles were complexed with said CPP-peptide or Cholesterol-conjugated peptide by incubating same for approximately 15 min at 37° C.

In yet another preferred embodiment said modified enveloped virus is provided with at least one anti-tumor, tumor-specific peptide that is MHC-I specific and so elicits an immune response ideally via MHC-I presentation on antigen presenting cells (APCs) for the activation of T-effector cells, named $CD8^+$ T cells, specifically cytotoxic T cell lymphocytes (CTLs).

Additionally or alternatively, said modified enveloped virus is provided with at least one anti-tumor, tumor-specific peptide that is MHC-II specific and so elicits an immune response ideally via MHC-II presentation on antigen presenting cells (APCs) for the activation of a $CD4^+$ (T-helper) cell response.

Accordingly, this invention also enables the use of different MHC-II epitopes coated onto the viral envelope to boost, alone or in combination with MHC-I epitopes, the immune response of the individual.

Additionally or alternatively the invention also enables the use of a peptide that (s) comprise(s) a fusion molecule including a plurality of different antigens.

Yet more preferably, there is provided a combination of different of said modified enveloped viruses where said viruses are selected from the group comprising Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus. Thus the invention concerns the use of at least two of any of the afore viruses and also extends to the use of a combination of any 3, 4, 5, 6 or 7 of the afore viruses.

Accordingly, the invention concerns the use of two different virus types or viral backbones enabling the Prime-Boost immunovirotherapy method where the treatment with a Prime (priming) virus of a particular species/genus coated with said peptides is followed by a treatment with Boost (boosting) virus of another particular species/genus (an immunologically distinct virus) coated with the same said peptides. The Prime-Boost immunovirotherapy method can dramatically further increase the tumor-specific T-cell immune responses by directing the majority of the immune responses created by the Prime-Boost method towards the said peptides.

When working the invention an enveloped virus modified as herein described may be used in the Prime-Boost immunovirotherapy in combination with another enveloped virus modified as herein described but presenting the same peptides or any other virus, such as an adenovirus, that has also been modified, including genetically or non-genetically, to present the same peptides.

Those skilled in the art will appreciate that since an enveloped virus, namely Herpes Simplex Virus 1 (HSV-1) is the most studied oncolytic enveloped virus and an engineered form of HSV-1 called T-VEC (Imlygic) is the first oncolytic virus showing efficacy in Phase III clinical trials and is the first oncolytic virus approved by both FDA and EMEA for the treatment of inoperable melanoma, it is critically important to introduce novel ways of boosting the anti-tumor immunity at the expense of the anti-viral immunity of these therapeutic and clinically approved viruses.

According to a second aspect of the invention there is therefore provided a pharmaceutical composition comprising:

1) a modified enveloped virus selected from the group comprising Herpes Simplex Virus 1 (HSV-1), Herpes Simplex Virus 2 (HSV-2), Vaccinia, Vesicular stomatitis Indiana virus (VSV), Measles Virus (MeV), Maraba viris and New Castle Disease (NDV) virus wherein said virus has at least one anti-tumor, tumor-specific peptide non-genetically attached to or inserted in/through the viral envelope; and 2) a suitable carrier.

According to a third aspect of the invention there is therefore provided a method for treating a cancer comprising exposing an individual to a modified enveloped virus selected from the group comprising Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus wherein said virus has at least one anti-tumor, tumor-specific peptide non-genetically attached to or inserted in/through the viral envelope.

More preferably still, said method involves, after a selected period, exposing said individual to another modified enveloped virus selected from the group comprising Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus wherein said virus has at least one anti-tumor, tumor-specific peptide non-genetically attached to or inserted in/through the viral envelope and further wherein said virus is different from the one used for the prior exposure. Alternatively, in the Prime-Boost immunovirotherapy said method involves, after a selected period, exposing said individual to any another virus, such as an adenovirus, that has also been modified, including genetically or non-genetically, to present the same peptides. Alternatively, yet again, said method may be practiced by first using any virus that has been modified in any way, including genetically or non-genetically, to express selected peptides, followed by using the modified virus of the invention, having the same peptides, to provide the booster therapy.

In this way Prime-Boost immunovirotherapy can be practiced.

Ideally, said step of exposing an individual to a virus includes intratumoral, intranodal, intraperitoneal or intravenous injection.

Most preferably the cancer referred to herein includes any one or more pf the following cancers: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In a further embodiment of the invention, either after exposing an individual to a modified virus that expresses at least one anti-tumor, tumor-specific peptide or after exposing said individual to an enveloped virus selected from the group comprising Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus wherein said virus has the same or a majority of the same of said peptide(s) non-genetically attached to or inserted in/through the viral envelope, exposing said individual to a checkpoint inhibitor. The check point inhibitor inhibits immune checkpoint molecules such as PD-1, PD-L1 and CTLA-4, In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

BRIEF DESCRIPTION OF THE DRAWINGS

An embodiment of the present invention will now be described by way of example only with reference to the following wherein:

FIG. 1 is a summary of the data we have obtained when the anti-tumor, tumor-specific peptide is attached to different viral envelopes using either a CPP or a cholesterol-conjugated peptide;

FIG. 2 shows CPP-containing peptides can be attached to the envelope of Herpes Simplex Virus 1. CPP containing and FITC-labelled peptide was complexed with HSV-1 and a sandwich ELISA was used for detection of the complexes. An anti-HSV-1 antibody was coated to the bottom of 96-well plate and PeptiENV complexes were incubated in the wells. After washing the unbound fraction, an anti-FITC HRP-conjugated antibody was used for the detection of the PeptiENV complex. FIG. 2 lower panel shows CPP-containing peptides have reduced diffusion time when complexed with HSV-1. Fluorescence correlation spectroscopy was used to analyze the diffusion kinetics of peptides complexed with HSV-1.

FIG. 3 middle panel shows cholesterol-containing peptides can be attached to the envelope of Vaccinia virus. Cholesterol-containing and FITC-labelled peptides were complexed with Vaccinia virus and a sandwich ELISA was used for the detection of the complexes. An anti-Vaccinia virus antibody was coated to the bottom of 96-well plate and PeptiENV complexes were incubated in the wells. After washing the unbound fraction, an anti-FITC HRP-conjugated antibody was used for the detection of the PeptiENV complexes. FIG. 3 lower panel shows cholesterol-containing SIINFEKL-peptides are readily presented by dendritic cells. Mouse splenocytes were pulsed with cholesterol-containing SIINFEKL-peptides and the presentation of MHCI epitope SIINFEKL by CD11c positive DC-population was determined by flow cytometry.

FIG. 4 middle panel shows CPP-containing peptides can be attached to the envelope Vaccinia virus. CPP-containing and FITC-labelled peptide was complexed with Vaccinia virus and a sandwich ELISA was used for the detection of the complexes. An anti-Vaccinia virus antibody was coated to the bottom of 96-well plate and PeptiENV complexes were incubated in the wells. After washing the unbound fraction, an anti-FITC HRP-conjugated antibody was used for the detection of the PeptiENV complex. FIG. 4 lower panel shows CPP-containing SIINFEKL-peptides are readily presented by dendritic cells. Mouse splenocytes were pulsed with CPP-containing SIINFEKL-peptides and the presentation of MHCI epitope SIINFEKL by CD11c positive DC-population was determined by flow cytometry.

FIG. 5 upper panel shows PeptiENV can induce DC activation even with very low virus amount. Vaccinia virus was complexed with CPP- or cholesterol-containing SIINFEKL-peptides and used for infection of mouse splenocytes. Two hours post-infection dendritic cells were analyzed by flow cytometry for the expression of DC activation markers. FIG. 5 lower panel shows PeptiENV can induce the presentation of specific anti-tumor MHC class I epitopes by the CD11c-positive DCs even with very low virus amount. Vaccinia virus was complexed with CPP- or cholesterol-containing SIINFEKL-peptides and used for infection of mouse splenocytes. After two hours the presentation of MHCI epitope SIINFEKL by CD11c positive DC-population was determined by flow cytometry.

FIG. 7 shows a schematic presentation of A) a cholesterol-conjugated immunomodulatory peptide and B) an immunomodulatory peptide having N-terminal cell penetrating peptide sequence. Color code for different functional sequences of the entities: In dark gray: cholesterol (A.) or cell penetrating sequence (B.). In red: cathepsin D/E cleavage site. In blue: furin cleavage site. In green: immunoproteasome processing sites. In black: the MHC-I restricted epitope.

Figure 9:
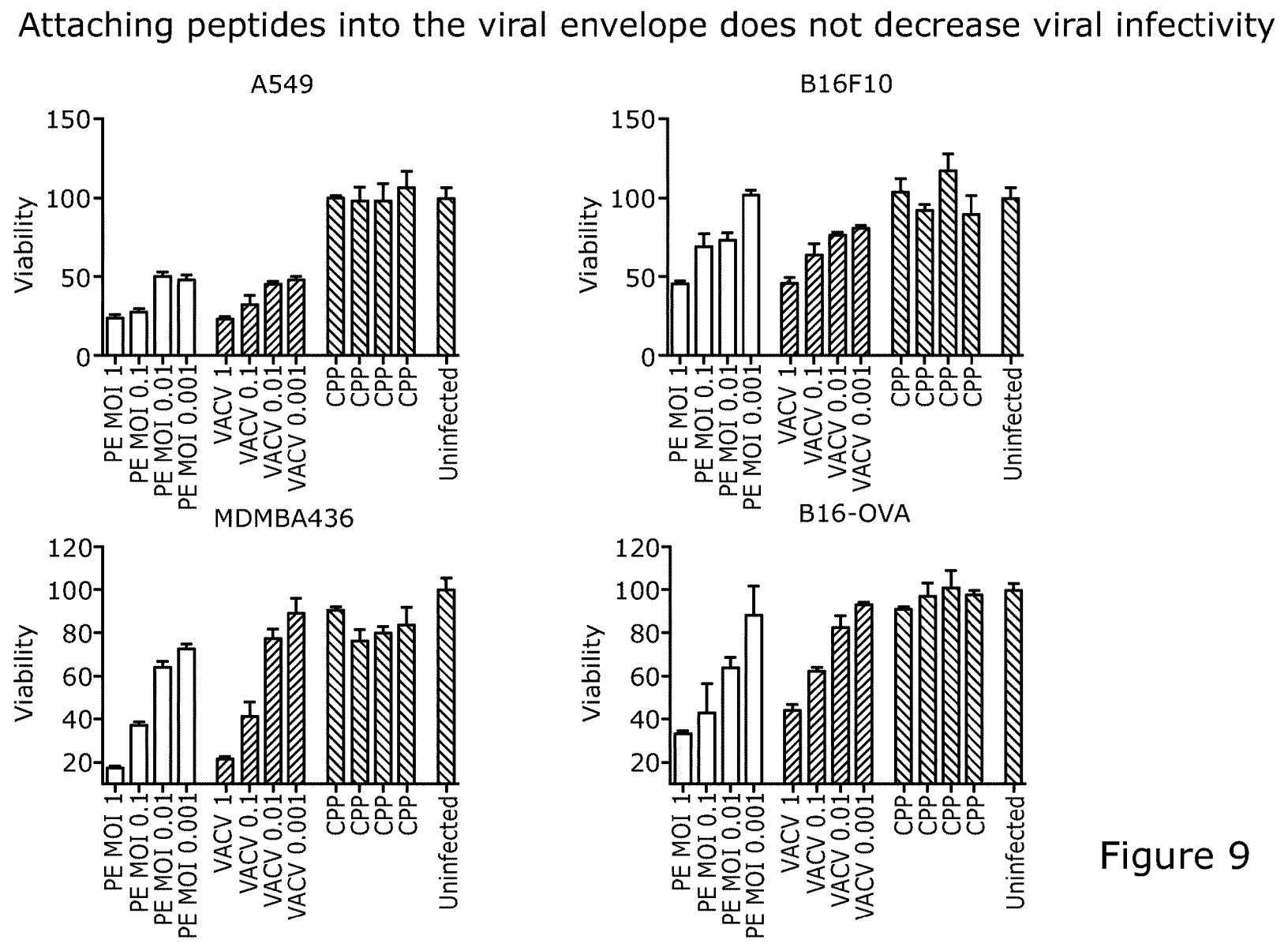

FIG. 9 shows CPP-containing peptides do not have any antiviral effects and can be safely attached to the viral envelope without loss of infectivity or oncolytic effect. Four different cell lines, A549, MDMBA436, B16F10 and B16-OVA, were tested for viral infectivity and PeptiENV was compared to non-modified virus.

Figure 13:
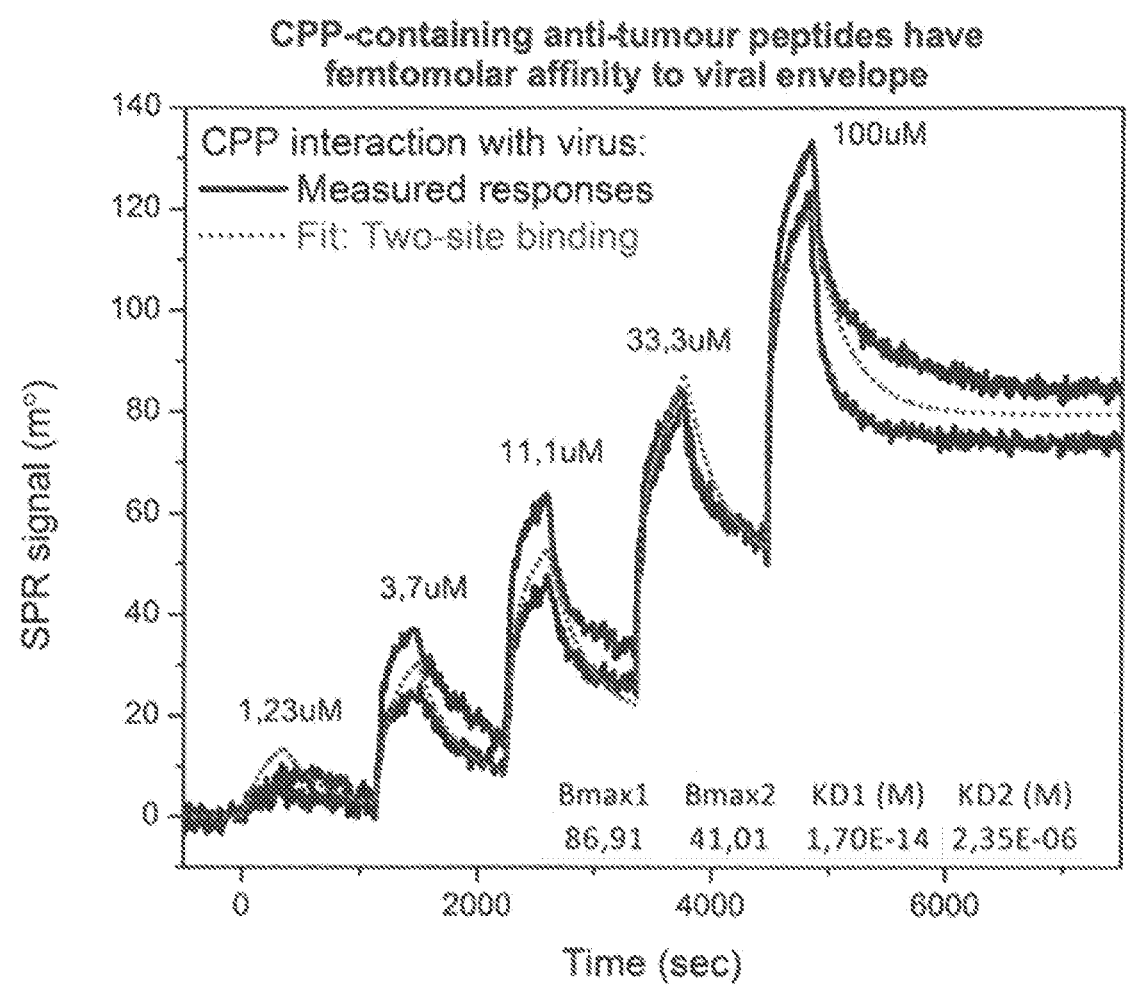

FIG. 13 shows surface plasmon resonance (SPR) measurements to confirm the high affinity of CPP-containing anti-tumor peptides to the viral envelope. Two-site binding kinetic fit model was used for the analysis of the SPR data.

DETAILED DESCRIPTION

Figure 3:
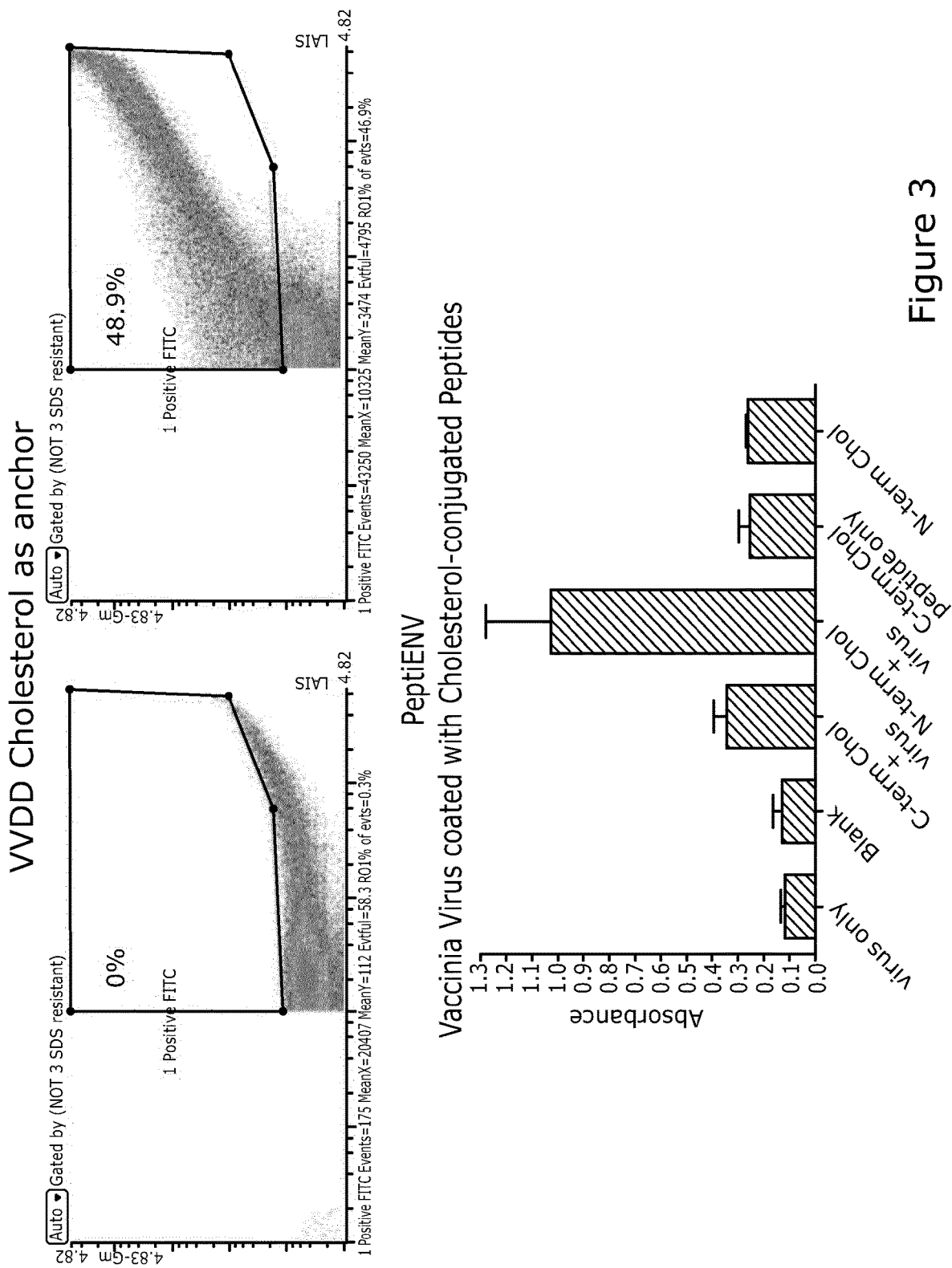
FIG. 3 upper panel shows cholesterol-containing peptides can be attached to the envelope of Vaccinia virus. Cholesterol-containing and FITC-labelled peptides were complexed with Vaccinia virus. After the purification of the PeptiENV complexes by 36% sucrose cushion and ultracentrifugation, the purified complexes were analyzed by flow cytometry. A. Vaccinia virus without complexed peptides and B. Vaccinia virus complexed with cholesterol containing FITC-labelled peptides.
Figure 3:
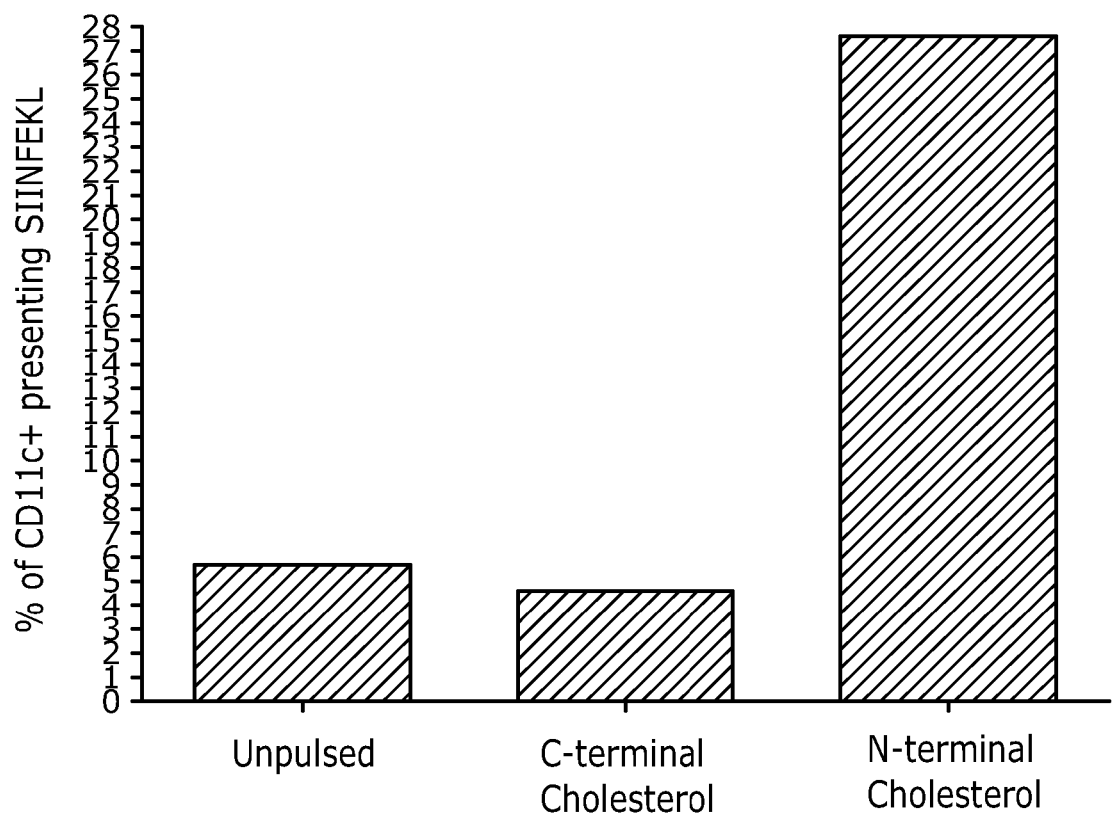
Figure 4:
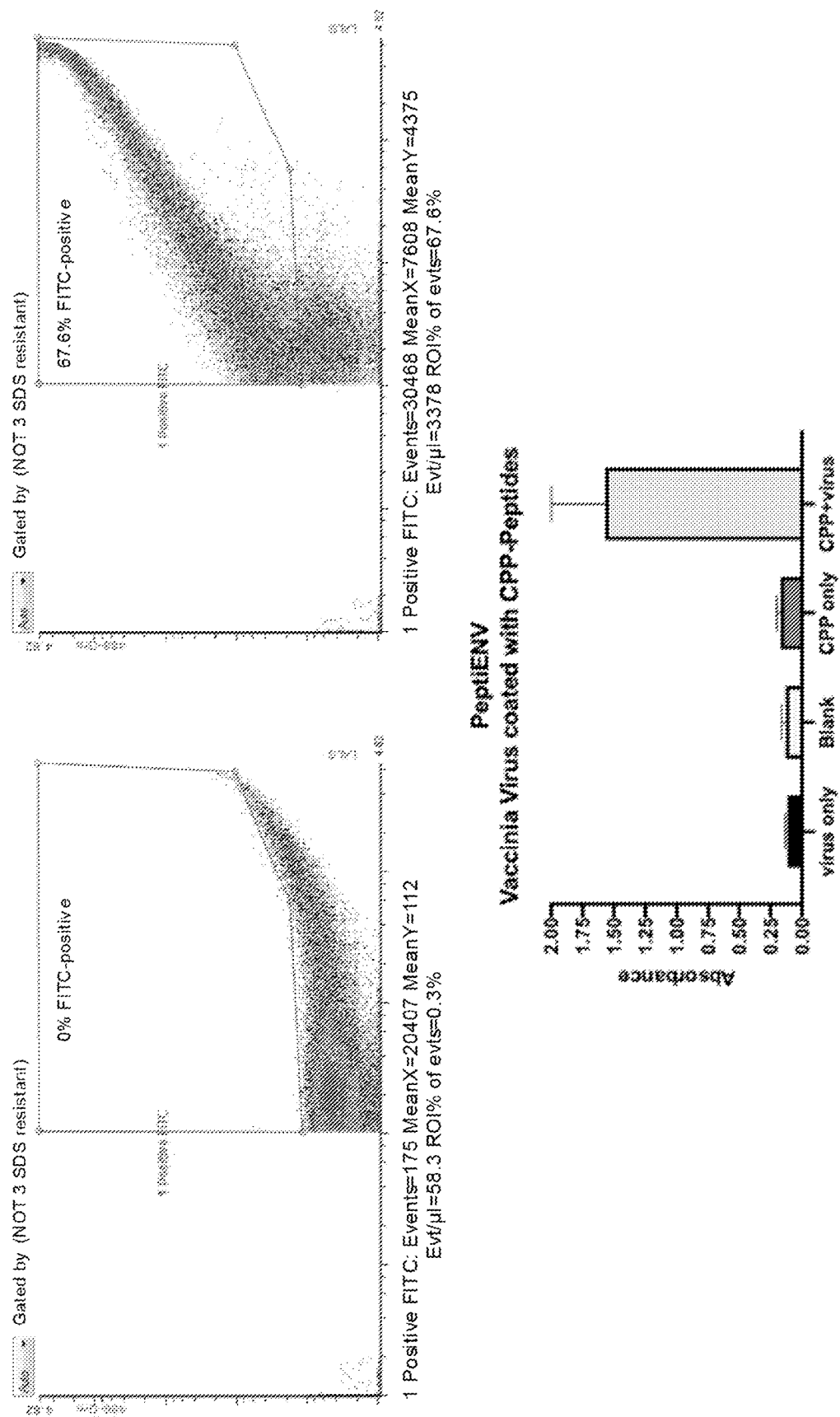
FIG. 4 upper panel shows CPP-containing peptides can be attached to the envelope of Vaccinia virus. CPP-containing and FITC-labelled peptides were complexed with Vaccinia virus. After the purification of the PeptiENV complexes by 36% sucrose cushion and ultracentrifugation, the purified complexes were analyzed by flow cytometry. A. HSV-1 without complexed peptides and B. HSV-1 complexed with CPP-containing FITC-labelled peptides.
Figure 4:
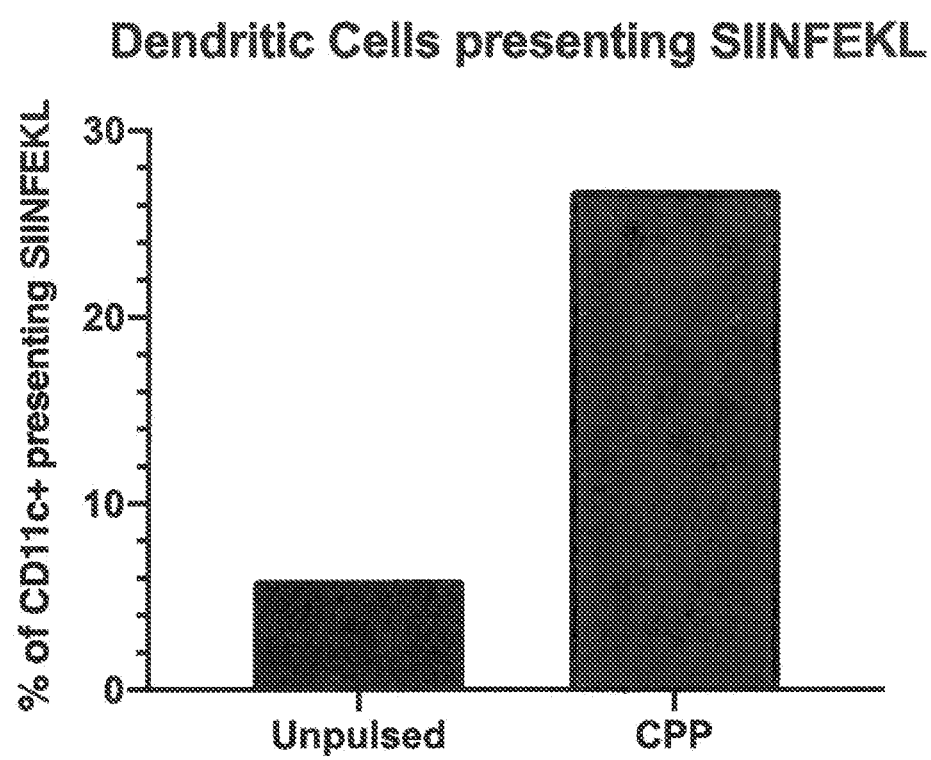
Figure 6:
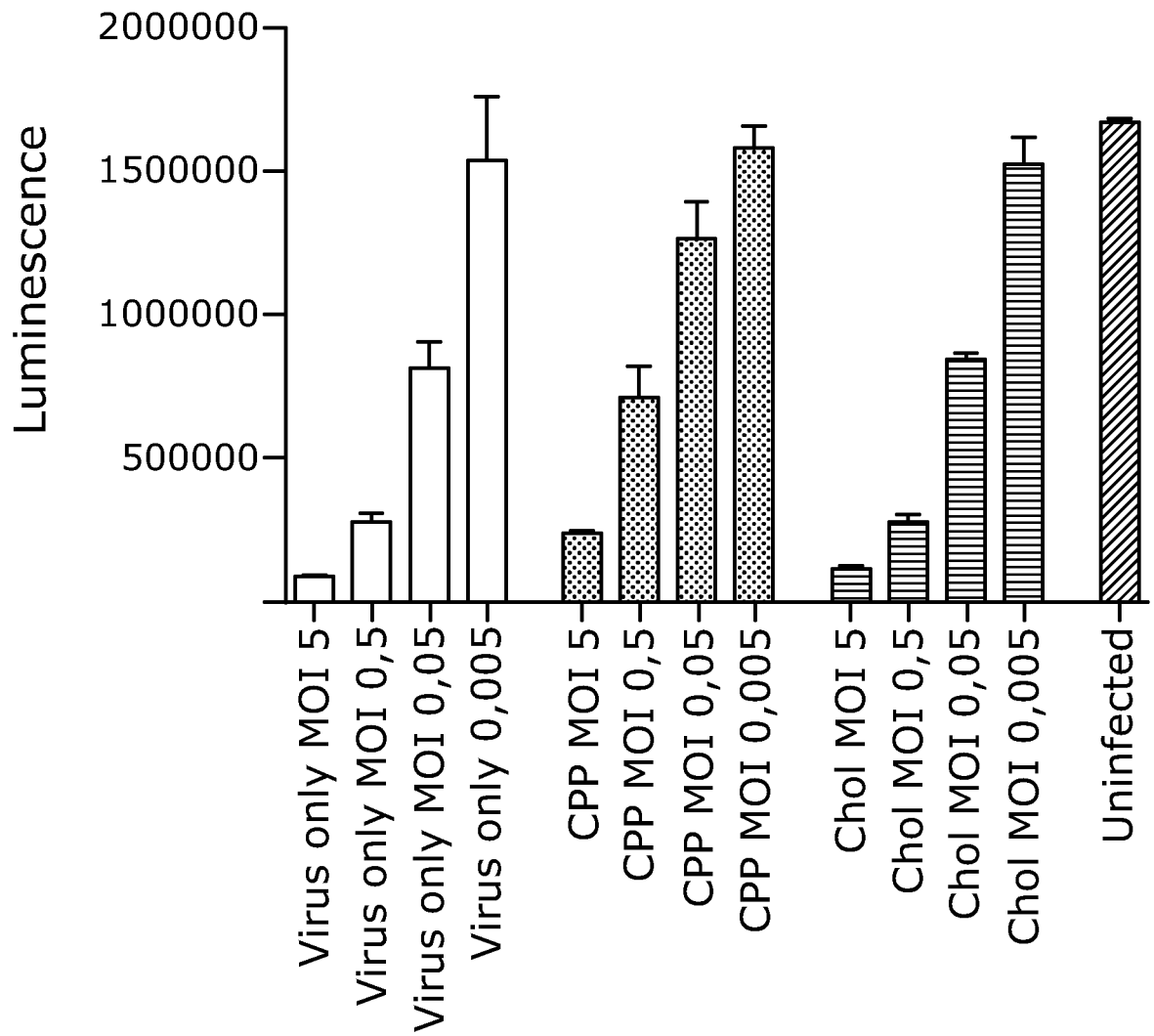
FIG. 6 shows PeptiENV virus-peptide complexation has no effect on viral infectivity. Infectivity of PeptiENV was compared with normal non-complexed virus and cell viability was measured 3 days post-infection.
Figure 8:
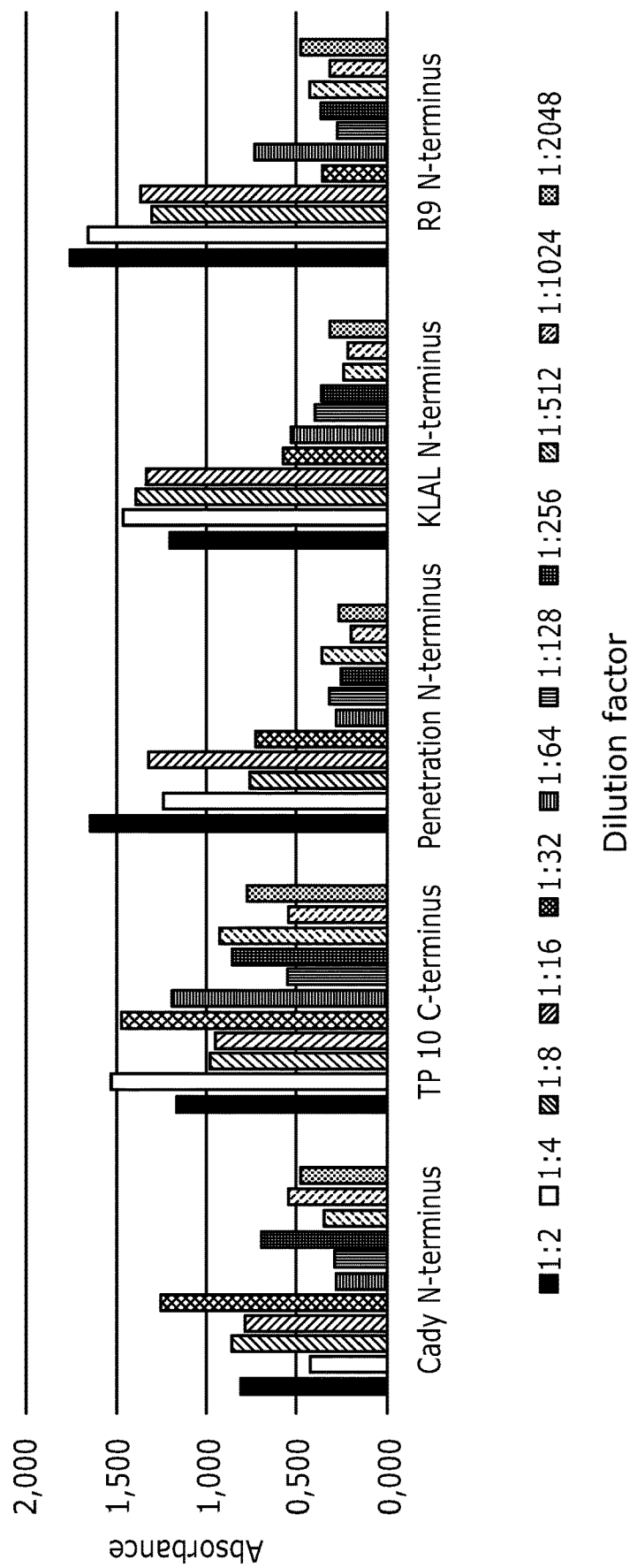
FIG. 8 shows that a variety of different CPP-sequences can be used to attach the anti-tumor peptides into the viral envelope. CPP-containing and FITC-labelled peptides were complexed with Vaccinia virus and a sandwich ELISA was used for the detection of the complexes. An anti-Vaccinia virus antibody was coated to the bottom of 96-well plate and PeptiENV complexes were incubated in the wells. After washing the unbound fraction, an anti-FITC HRP-conjugated antibody was used for the detection of the PeptiENV complexes.
Figure 10:
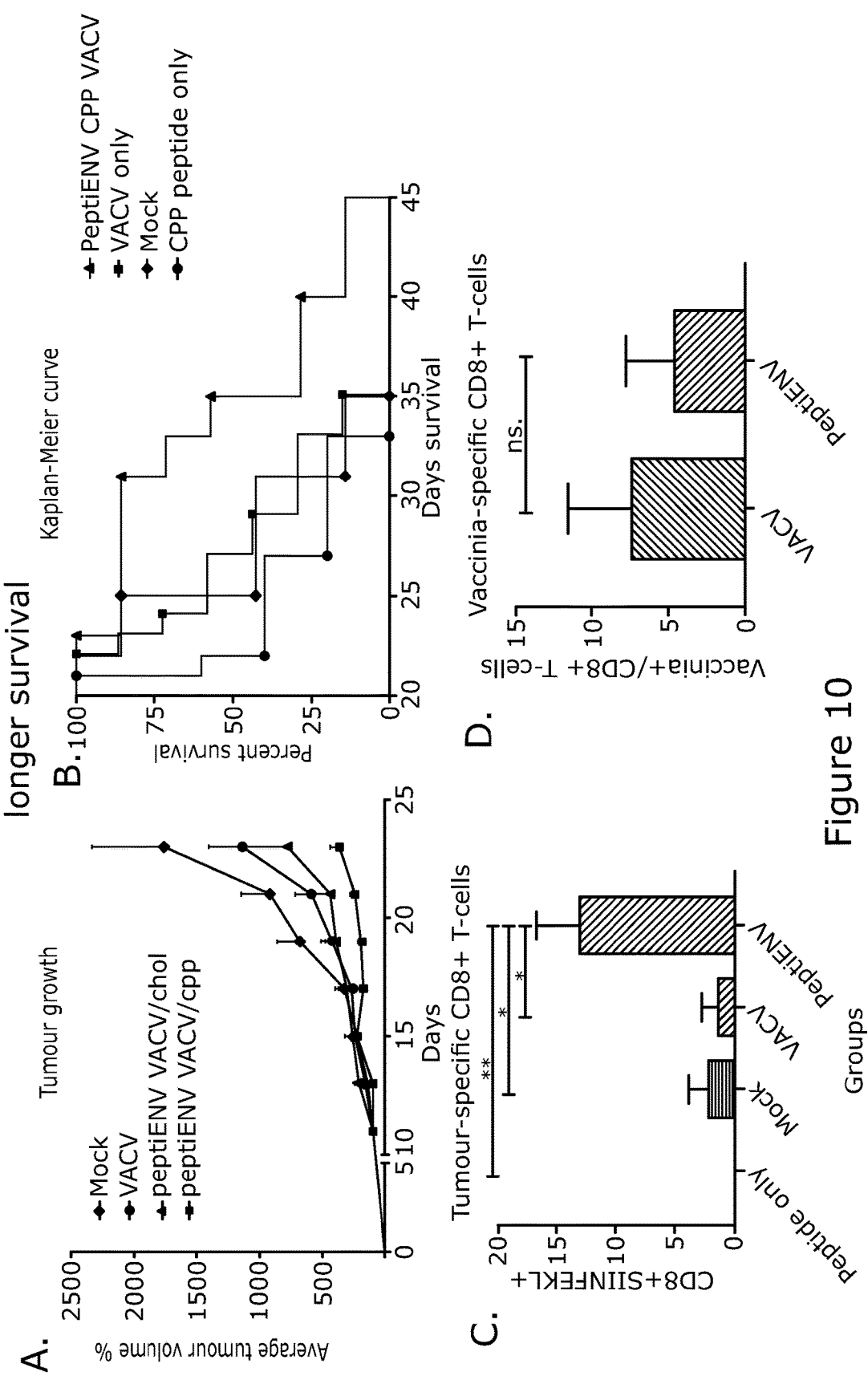
FIG. 10 shows anti-tumour peptides anchored into viral envelope by CPP- or Cholesterol moieties induce extensive anti-tumor immunity leading to enhanced control of tumor growth and longer survival. A. Comparison of tumor growth between groups of Mock (treated with injection media only), Vaccinia virus only, PeptiENV with anti-tumor peptides attached to the viral envelope with a cholesterol moiety (PeptiENV VACV/chol) and PeptiENV with anti-tumor peptides attached to the viral envelope with a CPP moiety (PeptiENV VACV/cpp). B. Kaplan-Meier survival curve of groups of mice treated with PeptiENV VACV/cpp, Vaccinia virus only, anti-tumor peptide alone (without virus) or Mock. C. Flow cytometric analysis of tumor-specific T-cells in treated tumor. PeptiENV can induce extensive filtration of tumor-specific effector T-cells in to the tumor microenvironment. D. Flow cytometric analysis of virus-specific T-cells in the tumor microenvironment. PeptiENV induces anti-viral immunity comparable to non-modified Vaccinia virus, while specifically inducing extensive anti-tumor immunity not presented by the non-modified Vaccinia virus.
Figure 11:
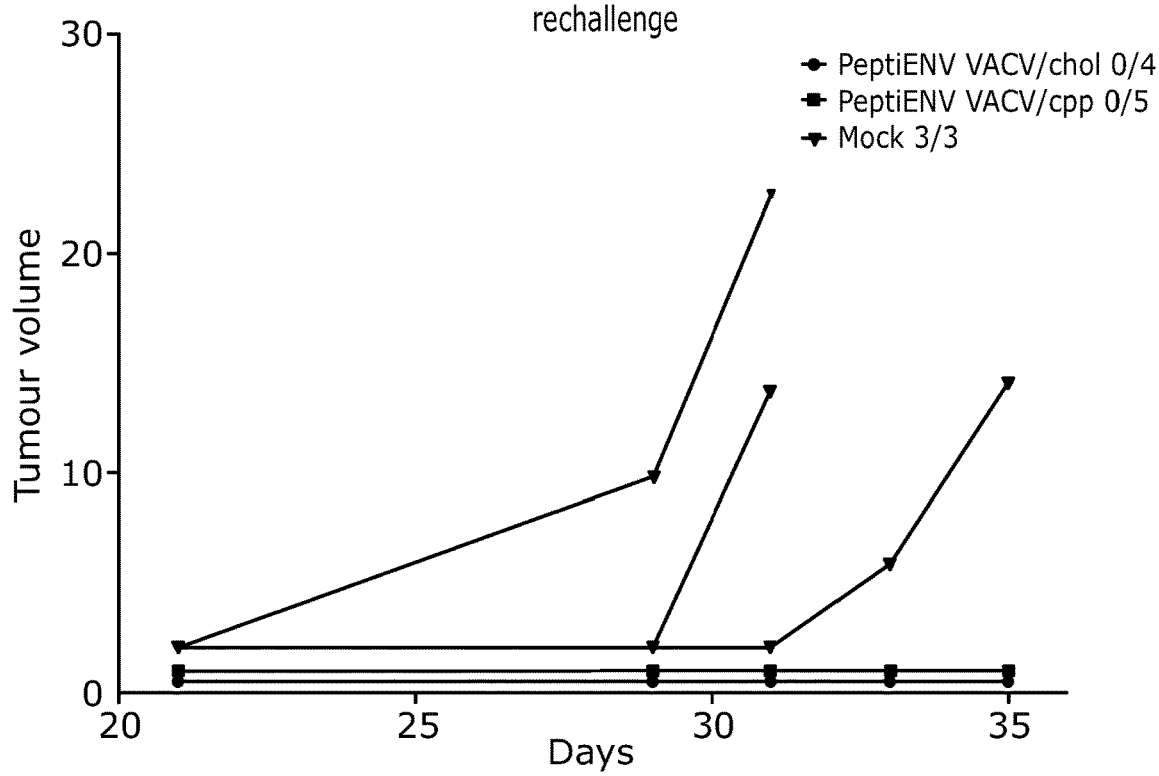
FIG. 11 shows PeptiENV VACV/chol and PeptiENV VACV/cpp treated mice elicit strong anti-tumor immune response and are protected from tumor rechallenge while Mock-treated mice are not protected. 500000 B16-OVA cells were injected into the opposite flank of the previous tumor implantation and mice where followed for 14 days. No tumor growth was observed in mice treated with PeptiENV while the tumor incidence was 100% in the Mock treated group.
Figure 12:
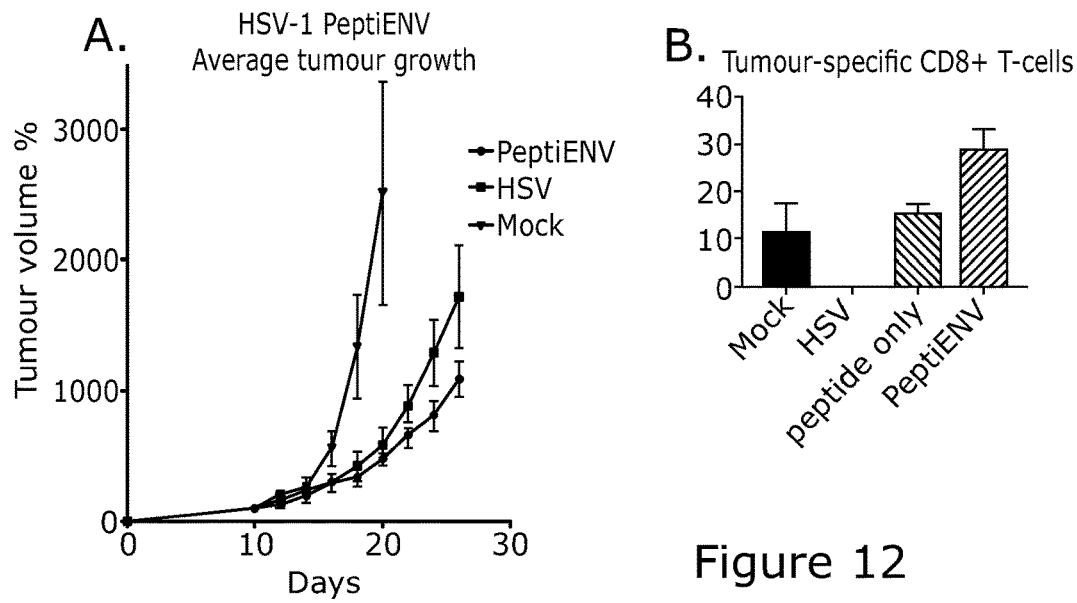
FIG. 12 shows anti-tumor peptides anchored into Herpes simplex virus 1 (HSV-1) envelope by CPP moiety induce strong anti-tumor immunity leading to enhanced control of tumor growth. A. Tumor growth curve of PeptiENV HSV-1/cpp, HSV-1 only and Mock treated groups. B. Flow cytometric analysis of tumor-specific T-cells in treated tumor. PeptiENV can induce extensive filtration of tumor-specific effector T-cells in to the tumor microenvironment.

Materials and Methods:
Peptides:
Peptides used in this study are listed below and were all purchased from PepScan:

```
CPP peptides:
                                          (SEQ ID NO: 8)
GRKKRRQRRRPQRVRRALISLEQLESIINFEKLTEW (SEQ ID NO: 24)
GRKKRRQRRRPQRVRRALISLEQLESIINFEKLTEW-FITC
```

-continued

RQIKIWFQNRRMKWKKRWEKISIINFEKLYKLK-FITC (SEQ ID NO: 25)

KLALKLALKALKAALKLARWEKISIINFEKLYKLK-FITC (SEQ ID NO: 26)

RRRRRRRRRWEKISIINFEKLYKLK-FITC (SEQ ID NO: 27)

FITC-RWEKISIINFEKLYKLRRRRRRRRR (SEQ ID NO: 28)

FITC-RWEKISIINFEKLYKLKETWWETWWTEWSQPKKKRKV (SEQ ID NO: 29)

FITC-RWEKISIINFEKLYKLAGYLLGKINLKALAALAKKIL (SEQ ID NO: 30)

GLWRALWRLLRSLWRLLWRARWEKISIINFEKLYKLK-FITC (SEQ ID NO: 31)

GRKKRRQRRRPQRWEKISIINFEKL (SEQ ID NO: 17)

GRKKRRQRRRPQRWEKISIINFEKLYKLRWEKISIINFEKL (SEQ ID NO: 18)

Cholesterol-conjugated peptides:

LEQLESIINFEKLTEWRVRRALISC-cholesterol (SEQ ID NO: 19)

FITC-LEQLESIINFEKLTEWRVRRALISC-cholesterol (SEQ ID NO: 32)

cholesterol-CRVRRALISLEQLESIINFEKLTEW (SEQ ID NO: 20)

cholesterol-CRVRRALISLEQLESIINFEKLTEW-FITC (SEQ ID NO: 33)

cholesterol-CSIINFEKL (SEQ ID NO: 21)

cholesterol-CRWEKISIINFEKL (SEQ ID NO: 22)

cholesterol-CRWEKISVYDFFVWLYKLRWEKISIINFEKL (SEQ ID NO: 23)

Cell Lines

Human lung carcinoma cell line A549, African Green monkey kidney epithelial cell line Vero (B) and Murine melanoma cell lines B16/OVA and B16-F10 were cultured in DMEM with 10% foetal calf serum (FBS) (Life Technologies) 1% L-glutamine and 1% penicillin/streptomycin at 37° C./5% CO2. Human triple negative breast cancer cell line MDMBA436 was cultured in RPMI with 10% foetal calf serum (FBS) (Life Technologies) 1% L-glutamine and 1% penicillin/streptomycin at 37° C./5% CO2.

Production of Viruses

Herpes simplex virus 1 was produced in Vero cells and purified with sucrose gradient ultracentrifugation and eluted in 20 mM MES, 100 mM NaCl, 30 mM Tris-HCl (pH 7.2). Western reserve strain of Vaccinia virus (VVDD-mDAI-RFP) was produced in A549 cells and purified through 36% sucrose cushion ultracentrifugation and eluted in 1 mM Tris (pH 9.0).

ELISAs $2.5 \times 10^7$ Vaccinia virus particles were complexed with 8ug of either CPP-peptide-FITC or cholesterol-conjugated peptide-FITC in 100 ul of DMEM for 15 min at 37° C. After complexation, unbound peptides were removed by ultracentrifugation (20.000 g, 40-80 mins) through 36% sucrose cushion in 1 mM Tris (pH 9.0). For ELISA, anti-Vaccinia polyclonal antibody (Abcam) was coated o/n at 4° C. into maxisorb 96-well immunoplates at the concentration of 2 ug/ml. Vaccinia-peptide complexes were incubated for 30-60 min at 37° C. or RT and washed with 1×PBS for three times. Complexes were detected with anti-FITC antibody conjugated to horseradish peroxidase (Abcam) (1:5000 dilution in 2% BSA-PBS). $2.5 \times 10^7$ Herpes simplex 1 virus particles were complexed with 8ug of either CPP-peptide-FITC or cholesterol-conjugated peptide-FITC in 100 ul of DMEM for 15 min at 37° C. For ELISA, anti-HSV-1 polyclonal antibody (Abcam) was coated o/n at 4° C. into maxisorb 96-well immunoplates at the concentration of 2 ug/ml. HSV-1-peptide complexes were incubated for 30-60 min at 37° C. or RT and washed with 1×PBS for three times. Complexes were detected with anti-FITC antibody conjugated to horseradish peroxidase (Abcam) (1:5000 dilution in 2% BSA-PBS).

Flow Cytometry $5 \times 10^7$ Vaccinia virus particles were complexed with 24 ug of either CPP-peptide-FITC or cholesterol-conjugated peptide-FITC in 200 ul of DMEM for 15 min at 37° C. After complexation, unbound peptides were removed by ultracentrifugation (20.000 g, 40-80 mins) through 36% sucrose cushion in 1 mM Tris (pH 9.0) and eluted to 2% Formalin in PBS. After fixing, formalin was removed with another ultracentrifugation (20.000 g, 40-80 mins) through 36% sucrose cushion and pellet was eluted to 1× ultrapure PBS (Gibco). Flow cytometry was performed with Apogee A50 Micro Flow Cytometer (Apogee) and FITC detection was used for assessing the complexes.

Cross-Presentation Experiments $2 \times 10^6$ spleenocytes in 800 μL of 10% RPMI-1640 culture media were incubated with 200 μL of GRKKRRQRRRPQRVRRALISLEQLESIINFEKLTEW (SEQ ID NO: 8), LEQLESIINFEKLTEWRVRRALISC-cholesterol (SEQ ID NO: 19) or cholesterol-CRVRRAL-ISLEQLESIINFEKLTEW (SEQ ID NO: 20) peptide dilution (0.19 μg/μL).

The vaccinia-peptide complexes were prepared as described for ELISAs. After 2 h of incubation cells were washed and stained with either APC anti-mouse H-2Kb bound to SIINFEKL or APC Mouse IgG1, κ Isotype Ctrl (BioLegend, San Diego, Calif., USA), and the samples were analyzed by flow cytometry.

Cell Viability Assay

Cell viability was measured using the CellTiterGlo 96 AQueous One Solution Cell Proliferation Assay (Promega), and a multi-well plate reader (Varioscan; ThermoLabsystems) to determine the luminescence of the samples.

Surface Plasmon Resonance

Measurements were performed using a multi-parametric SPR Navi™ 220A instrument (Bionavis Ltd, Tampere, Finland). Phosphate buffered saline (PBS) (pH 7.4) was used as a running buffer. A constant flow rate of 20 μL/min was used throughout the experiments, and temperature was set to +20° C. Laser light with a wavelength of 670 nm was used for surface plasmon excitation.

A sensor slide with a silicon dioxide surface was activated by 5 min of plasma treatment followed by coating with APTES ((3-aminopropyl)triethoxysilane) by incubating the sensor in 50 mM APTES in isopropanol for 4 h. The sensor was then washed and placed into the SPR device, and viruses were immobilized in situ on the sensor surface of the two test channels by injecting $1.1 \times 10^7$ pfu of VACV in PBS (pH 7.4) for approximately 12 min, followed by a 3-min wash with PBS. CPP-containing anti-tumor peptide or peptide without CPP sequence (non-interacting control) was then injected into both flow channels of the flow cell in parallel, with increasing peptide concentrations ranging from 1.23 uM to 100 uM.

Animal Experiments

C57BL/6JOIaHsd-mouse strain was used in all animal experiment. 350000 B16-OVA-cells were injected in the right flank of mice (in rechallence experiment, cells were injected in to the left flank) and when the tumor size reached approximately 50 mm$^3$ (10-12 days after injection) mice were treated with non-modified viruses, PeptiENV-platform, peptides only or injection media only (Mock). Mice were treated on day 0, 2 and then a booster treatment was given on day 8-10. Tumors were measured every second day until the tumor size reached the maximum allowed.

The invention claimed is:

1. A modified enveloped virus selected from the group consisting of comprising Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus wherein said virus has at least one anti-tumor, tumor-specific peptide non-genetically attached to or inserted in/through the viral envelope, further wherein the peptide has a length selected from the group consisting of: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 amino acids.

2. The modified enveloped virus according to claim 1 wherein a plurality of said peptides are non-genetically attached to or inserted in/through the viral envelope.

3. The modified enveloped virus according to claim 2 wherein:
said peptides are identical; or
said peptides have greater than 90%, 91%, 92%, 93%, 94%, 95%, 96%, 97%, 98%, or 99% sequence identity with each other; or
said peptides are representative of a number of different antigens.

4. The modified enveloped virus according to claim 1 wherein said peptide(s) is/are MHC-I restricted.

5. The modified enveloped virus according to claim 1 wherein said peptide(s) is/are MHC-II restricted.

6. The modified enveloped virus according to claim 2 wherein said peptides comprise a mix of MHC-I restricted peptides and MHC-II restricted peptides.

7. The modified enveloped virus according to claim 1 wherein said peptide(s) comprise(s) a fusion molecule including a plurality of different antigens.

8. The modified enveloped virus according to claim 1 wherein said peptide also comprises at least one cleavage site.

9. The modified enveloped virus according to claim 1 wherein said peptide also comprises at least one immunoproteasome processing site.

10. The modified enveloped virus according to claim 1 wherein said peptide is positioned between a pair of immunoproteasome processing sites and upstream or downstream thereof is at least one cleavage site.

11. The modified enveloped virus according to claim 1 wherein said peptide(s) are non-covalently attached to or inserted in/through the viral envelope.

12. The modified enveloped virus according to claim 1 wherein said peptide(s) is/are non-genetically attached to or inserted in/through said viral envelope using either a cell penetrating peptide or a cholesterol-conjugated peptide.

13. The modified enveloped virus according to claim 1 wherein said peptide(s) is/are non-genetically attached to or inserted in/through said viral envelope using either a cell penetrating peptide or a cholesterol-conjugated peptide selected from the group consisting of:
GRKKRRQRRRPQ (SEQ ID NO: 1), CPP sequence in the N- or C-terminus of the said antitumor, tumor-specific peptide;
RQIKIWFQNRRMKWKK (SEQ ID NO: 2), CPP sequence in the N- or C-terminus of the said anti-tumor, tumor-specific peptide;
KLALKLALKALKAALKLA (SEQ ID NO: 3), CPP sequence in the N- or C-terminus of the said anti-tumor, tumor-specific peptide;
RRRRRRRRR (SEQ ID NO: 4), CPP sequence in the N- or C-terminus of the said antitumor, tumor-specific peptide;
KETWWETWWTEWSQPKKKRKV (SEQ ID NO: 5), CPP sequence in the N- or C-terminus of the said anti-tumor, tumor-specific peptide;
AGYLLGKINLKALAALAKKIL (SEQ ID NO: 6), CPP sequence in the N- or C-terminus of the said anti-tumor, tumor-specific peptide;
AGLWRALWRLLRSLWRLLWRA (SEQ ID NO: 7), CPP sequence in the N- or C-terminus of the said anti-tumor, tumor-specific peptide; and a cholesterol moiety N- or C-terminus of the said anti-tumor, tumor-specific peptide.

14. The modified enveloped virus according to claim 13 wherein said peptide(s) is/are selected from the group consisting of:

```
                                             (SEQ ID NO: 8)
GRKKRRQRRRPQRVRRALISLEQLESIINTFEKLTEW;

(SEQ ID NO: 9)
RQIKIWFQNRRMKWKKRWEKISIINFEKLYKLK;

(SEQ ID NO: 10)
KLALKLALKALKAALKLARWEKISIINFEKLYKLK;

(SEQ ID NO: 11)
RRRRRRRRRWEKISIINFEKLYKLK;

(SEQ ID NO: 12)
RWEKISIINFEKLYKLRRRRRRRRR;

(SEQ ID NO: 13)
RWEKISIINFEKLYKLKETWWETWWTEWSQPKKKRKV;

(SEQ ID NO: 14)
RWEKISIINFEKLYKLAGYLLGKINTLKALAALAKKIL;

(SEQ ID NO: 15)
AGLWRALWRLLRSLWRLLWRA RWEKISIINFEKLYKLK;

(SEQ ID NO: 16)
GRKKRRQRRRPQRWEKISIINFEKLYKL;

(SEQ ID NO: 17)
GRKKRRQRRRPQRWEKISIINFEKL;

(SEQ ID NO: 18)
GRKKRRQRRRPQRWEKISIINFEKLYKLRWEKISIINFEKL;

(SEQ ID NO: 19)
LEQLESIINFEKLTEWRVRRALISC-cholesterol;

(SEQ ID NO: 20)
cholesterol-CRVRRALISLEQLESIINFEKLTEW;

(SEQ ID NO: 21)
cholesterol-CSIINFEKL;

(SEQ ID NO: 22)
cholesterol-CRWEKISIINFEKL;

(SEQ ID NO: 23)
cholesterol-CRWEKISVYDFFVWLYKLRWEKISIINFEKL;

(SEQ ID NO: 24)
GRKKRRQRRRPQRVRRALISLEQLESIINFEKLTEW-FITC;

(SEQ ID NO: 25)
RQIKIWFQNRRMKWKKRWEKISIINFEKLYKLK-FITC;

(SEQ ID NO: 26)
KLALKLALKALKAALKLARWEKISIINFEKLYKLK-FITC;
```

-continued

```
                                            (SEQ ID NO: 27)
RRRRRRRRRRWEKISIINFEKLYKLK-FITC;

(SEQ ID NO: 28)
FITC-RWEKISIINFEKLYKLRRRRRRRRR;

(SEQ ID NO: 29)
FITC-RWEKISIINFEKLYKLKETWWETWWTEWSQPKKKRKV;

(SEQ ID NO: 30)
FITC-RWEKISIINFEKLYKLAGYLLGKINLKALAALAKKIL
and (SEQ ID NO: 31)
GLWRALWRLLRSLWRLLWRARWEKISIINFEKLYKLK-FITC.
```

15. The modified enveloped virus according to claim 1 wherein there is provided a combination of different non-genetically modified enveloped viruses selected from the group consisting of Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus.

16. The modified enveloped virus according to claim 15 wherein said combination comprises any 2, 3, 4, 5, 6 or 7 of the afore viruses modified to comprise at least one anti-tumor, tumor-specific peptide non-genetically attached to or inserted in/through the viral envelope of said virus.

17. A pharmaceutical composition comprising: a modified enveloped virus according to claim 1 and a suitable carrier.

18. A method for treating a cancer comprising exposing an individual to a modified enveloped virus selected from the group consisting of Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus wherein said virus has at least one anti-tumor, tumor-specific peptide non-genetically attached to or inserted in/through the viral envelope, further wherein the peptide has a length selected from the group consisting of: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 amino acids.

19. The method according to claim 18 wherein said method further comprises, after a selected period, exposing said individual to another modified enveloped virus selected from the group consisting of Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus wherein said virus has said at least one anti-tumor, tumor-specific peptide non-genetically attached to or inserted in/through the viral envelope and further wherein said virus is different from the one used for the prior exposure.

20. The method according to claim 19 wherein said another modified enveloped virus is coated with the same or a majority of the same said peptides as the first modified enveloped virus.

21. The method according to claim 18 wherein after exposure to said one or more virus(es) said individual is further exposed to a checkpoint inhibitor.

22. A method for treating a cancer comprising exposing an individual to a modified virus that expresses at least one anti-tumor, tumor-specific peptide having a length selected from the group consisting of: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 amino acids and then, after a selected period, exposing said individual to an enveloped virus selected from the group consisting of Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus wherein said virus has the same or a majority of the same of said peptide(s) non-genetically attached to or inserted in/through the viral envelope.

23. The method according to claim 22 wherein either after exposing an individual to a modified virus that expresses at least one anti-tumor, tumor-specific peptide or after exposing said individual to an enveloped virus selected from the group consisting of Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus wherein said virus has the same or a majority of the same of said peptide(s) non-genetically attached to or inserted in/through the viral envelope, exposing said individual to a checkpoint inhibitor.

* * * * *

UNITED STATES PATENT AND TRADEMARK OFFICE
CERTIFICATE OF CORRECTION

PATENT NO.         : 10,982,194 B2
APPLICATION NO.    : 16/337220
DATED              : April 20, 2021
INVENTOR(S)        : Vincenzo Cerullo et al.

Page 1 of 1

It is certified that error appears in the above-identified patent and that said Letters Patent is hereby corrected as shown below:

In the Claims

Column 29, Claim 1, Line 3 - Please delete "comprising"

Column 30, Claim 14, Line 35 - Please delete "T"

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 33

<210> SEQ ID NO 1
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 1

Gly Arg Lys Lys Arg Arg Gln Arg Arg Arg Pro Gln
1               5                  10

<210> SEQ ID NO 2
<211> LENGTH: 16
<212> TYPE: PRT
<213> ORGANISM: Artificial Sequence
<220> FEATURE:
<223> OTHER INFORMATION: cell pentrating peptide

<400> SEQUENCE: 2

Arg Gln Ile Lys Ile Trp Phe Gln Asn Arg Arg Met Lys Trp Lys Lys
1               5                  10                  15

<210> SEQ ID NO 3
<211> LENGTH: 18
<212> TYPE: PRT
<213> ORGANISM: Artificial Sequence
<220> FEATURE:
<223> OTHER INFORMATION: cell pentrating peptide

<400> SEQUENCE: 3

Lys Leu Ala Leu Lys Leu Ala Leu Lys Ala Leu Lys Ala Ala Leu Lys
1               5                  10                  15

Leu Ala

<210> SEQ ID NO 4
<211> LENGTH: 9
<212> TYPE: PRT
<213> ORGANISM: Artificial Sequence
<220> FEATURE:
<223> OTHER INFORMATION: cell pentrating peptide

<400> SEQUENCE: 4

Arg Arg Arg Arg Arg Arg Arg Arg Arg
1               5

<210> SEQ ID NO 5
<211> LENGTH: 21
<212> TYPE: PRT
<213> ORGANISM: Artificial Sequence
<220> FEATURE:
<223> OTHER INFORMATION: cell pentrating peptide

<400> SEQUENCE: 5

Lys Glu Thr Trp Trp Glu Thr Trp Trp Thr Glu Trp Ser Gln Pro Lys
1               5                  10                  15
```

```
Lys Lys Arg Lys Val
        20

<210> SEQ ID NO 6
<211> LENGTH: 21
<212> TYPE: PRT
<213> ORGANISM: Artificial Sequence
<220> FEATURE:
<223> OTHER INFORMATION: cell pentrating peptide

<400> SEQUENCE: 6

Ala Gly Tyr Leu Leu Gly Lys Ile Asn Leu Lys Ala Leu Ala Ala Leu
1               5                   10                  15

Ala Lys Lys Ile Leu
        20

<210> SEQ ID NO 7
<211> LENGTH: 21
<212> TYPE: PRT
<213> ORGANISM: Artificial Sequence
<220> FEATURE:
<223> OTHER INFORMATION: cell pentrating peptide

<400> SEQUENCE: 7

Ala Gly Leu Trp Arg Ala Leu Trp Arg Leu Leu Arg Ser Leu Trp Arg
1               5                   10                  15

Leu Leu Trp Arg Ala
        20

<210> SEQ ID NO 8
<211> LENGTH: 36
<212> TYPE: PRT
<213> ORGANISM: Artificial Sequence
<220> FEATURE:
<223> OTHER INFORMATION: cell pentrating peptide

<400> SEQUENCE: 8

Gly Arg Lys Lys Arg Arg Gln Arg Arg Pro Gln Arg Val Arg Arg
1               5                   10                  15

Ala Leu Ile Ser Leu Glu Gln Leu Glu Ser Ile Ile Asn Phe Glu Lys
            20                  25                  30

Leu Thr Glu Trp
        35

<210> SEQ ID NO 9
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 9

Arg Gln Ile Lys Ile Trp Phe Gln Asn Arg Arg Met Lys Trp Lys Lys
1               5                   10                  15

Arg Trp Glu Lys Ile Ser Ile Ile Asn Phe Glu Lys Leu Tyr Lys Leu
            20                  25                  30

Lys

<210> SEQ ID NO 10
<211> LENGTH: 35
<212> TYPE: PRT
<213> ORGANISM: Artificial Sequence
<220> FEATURE:
<223> OTHER INFORMATION: cell penetrating peptide
```

```
<400> SEQUENCE: 10

Lys Leu Ala Leu Lys Leu Ala Leu Lys Ala Leu Lys Ala Ala Leu Lys
1               5                   10                  15

Leu Ala Arg Trp Glu Lys Ile Ser Ile Ile Asn Phe Glu Lys Leu Tyr
            20                  25                  30

Lys Leu Lys
        35

<210> SEQ ID NO 11
<211> LENGTH: 26
<212> TYPE: PRT
<213> ORGANISM: Artificial Sequence
<220> FEATURE:
<223> OTHER INFORMATION: cell penetrating peptide

<400> SEQUENCE: 11

Arg Arg Arg Arg Arg Arg Arg Arg Arg Trp Glu Lys Ile Ser Ile
1               5                   10                  15

Ile Asn Phe Glu Lys Leu Tyr Lys Leu Lys
            20                  25

<210> SEQ ID NO 12
<211> LENGTH: 25
<212> TYPE: PRT
<213> ORGANISM: Artificial Sequence
<220> FEATURE:
<223> OTHER INFORMATION: cell penetrating peptide

<400> SEQUENCE: 12

Arg Trp Glu Lys Ile Ser Ile Ile Asn Phe Glu Lys Leu Tyr Lys Leu
1               5                   10                  15

Arg Arg Arg Arg Arg Arg Arg Arg Arg
            20                  25

<210> SEQ ID NO 13
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 13

Arg Trp Glu Lys Ile Ser Ile Ile Asn Phe Glu Lys Leu Tyr Lys Leu
1               5                   10                  15

Lys Glu Thr Trp Trp Glu Thr Trp Trp Thr Glu Trp Ser Gln Pro Lys
            20                  25                  30

Lys Lys Arg Lys Val
        35

<210> SEQ ID NO 14
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 14

Arg Trp Glu Lys Ile Ser Ile Ile Asn Phe Glu Lys Leu Tyr Lys Leu
1               5                   10                  15

Ala Gly Tyr Leu Leu Gly Lys Ile Asn Leu Lys Ala Leu Ala Ala Leu
            20                  25                  30
```

```
Ala Lys Lys Ile Leu
        35

<210> SEQ ID NO 15
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 15

Ala Gly Leu Trp Arg Ala Leu Trp Arg Leu Leu Arg Ser Leu Trp Arg
1               5                   10                  15

Leu Leu Trp Arg Ala Arg Trp Glu Lys Ile Ser Ile Ile Asn Phe Glu
            20                  25                  30

Lys Leu Tyr Lys Leu Lys
        35

<210> SEQ ID NO 16
<211> LENGTH: 28
<212> TYPE: PRT
<213> ORGANISM: Artificial Sequence
<220> FEATURE:
<223> OTHER INFORMATION: cell penetrating peptide

<400> SEQUENCE: 16

Gly Arg Lys Lys Arg Arg Gln Arg Arg Arg Pro Gln Arg Trp Glu Lys
1               5                   10                  15

Ile Ser Ile Ile Asn Phe Glu Lys Leu Tyr Lys Leu
            20                  25

<210> SEQ ID NO 17
<211> LENGTH: 25
<212> TYPE: PRT
<213> ORGANISM: Artificial Sequence
<220> FEATURE:
<223> OTHER INFORMATION: cell penetrating peptide

<400> SEQUENCE: 17

Gly Arg Lys Lys Arg Arg Gln Arg Arg Arg Pro Gln Arg Trp Glu Lys
1               5                   10                  15

Ile Ser Ile Ile Asn Phe Glu Lys Leu
            20                  25

<210> SEQ ID NO 18
<211> LENGTH: 41
<212> TYPE: PRT
<213> ORGANISM: Artificial Sequence
<220> FEATURE:
<223> OTHER INFORMATION: cell penetrating peptide

<400> SEQUENCE: 18

Gly Arg Lys Lys Arg Arg Gln Arg Arg Arg Pro Gln Arg Trp Glu Lys
1               5                   10                  15

Ile Ser Ile Ile Asn Phe Glu Lys Leu Tyr Lys Leu Arg Trp Glu Lys
            20                  25                  30

Ile Ser Ile Ile Asn Phe Glu Lys Leu
        35                  40

<210> SEQ ID NO 19
<211> LENGTH: 25
<212> TYPE: PRT
<213> ORGANISM: Artificial Sequence
<220> FEATURE:
```

```
<223> OTHER INFORMATION: cell penetrating peptide
<220> FEATURE:
<221> NAME/KEY: MOD_RES
<222> LOCATION: (25)..(25)
<223> OTHER INFORMATION: Cholesterol

<400> SEQUENCE: 19

Leu Glu Gln Leu Glu Ser Ile Ile Asn Phe Glu Lys Leu Thr Glu Trp
1               5                   10                  15

Arg Val Arg Arg Ala Leu Ile Ser Cys
            20                  25

<210> SEQ ID NO 20
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Cholesterol

<400> SEQUENCE: 20

Cys Arg Val Arg Arg Ala Leu Ile Ser Leu Glu Gln Leu Glu Ser Ile
1               5                   10                  15

Ile Asn Phe Glu Lys Leu Thr Glu Trp
            20                  25

<210> SEQ ID NO 21
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Cholesterol

<400> SEQUENCE: 21

Cys Ser Ile Ile Asn Phe Glu Lys Leu
1               5

<210> SEQ ID NO 22
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Cholesterol

<400> SEQUENCE: 22

Cys Arg Trp Glu Lys Ile Ser Ile Ile Asn Phe Glu Lys Leu
1               5                   10

<210> SEQ ID NO 23
<211> LENGTH: 31
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Cholesterol
```

<400> SEQUENCE: 23

Cys Arg Trp Glu Lys Ile Ser Val Tyr Asp Phe Phe Val Trp Leu Tyr
1               5                   10                  15

Lys Leu Arg Trp Glu Lys Ile Ser Ile Ile Asn Phe Glu Lys Leu
            20                  25                  30

<210> SEQ ID NO 24
<211> LENGTH: 36
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (36)..(36)
<223> OTHER INFORMATION: FITC

<400> SEQUENCE: 24

Gly Arg Lys Lys Arg Arg Gln Arg Arg Pro Gln Arg Val Arg Arg
1               5                   10                  15

Ala Leu Ile Ser Leu Glu Gln Leu Glu Ser Ile Ile Asn Phe Glu Lys
            20                  25                  30

Leu Thr Glu Trp
        35

<210> SEQ ID NO 25
<211> LENGTH: 33
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (33)..(33)
<223> OTHER INFORMATION: FITC

<400> SEQUENCE: 25

Arg Gln Ile Lys Ile Trp Phe Gln Asn Arg Arg Met Lys Trp Lys Lys
1               5                   10                  15

Arg Trp Glu Lys Ile Ser Ile Ile Asn Phe Glu Lys Leu Tyr Lys Leu
            20                  25                  30

Lys

<210> SEQ ID NO 26
<211> LENGTH: 35
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (35)..(35)
<223> OTHER INFORMATION: FITC

<400> SEQUENCE: 26

Lys Leu Ala Leu Lys Leu Ala Leu Lys Ala Leu Lys Ala Ala Leu Lys
1               5                   10                  15

Leu Ala Arg Trp Glu Lys Ile Ser Ile Ile Asn Phe Glu Lys Leu Tyr
            20                  25                  30

Lys Leu Lys
        35

<210> SEQ ID NO 27

<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (26)..(26)
<223> OTHER INFORMATION: FITC

<400> SEQUENCE: 27

Arg Arg Arg Arg Arg Arg Arg Arg Arg Arg Trp Glu Lys Ile Ser Ile
1               5                   10                  15

Ile Asn Phe Glu Lys Leu Tyr Lys Leu Lys
            20                  25

<210> SEQ ID NO 28
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: FITC

<400> SEQUENCE: 28

Arg Trp Glu Lys Ile Ser Ile Ile Asn Phe Glu Lys Leu Tyr Lys Leu
1               5                   10                  15

Arg Arg Arg Arg Arg Arg Arg Arg Arg
            20                  25

<210> SEQ ID NO 29
<211> LENGTH: 37
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: FITC

<400> SEQUENCE: 29

Arg Trp Glu Lys Ile Ser Ile Ile Asn Phe Glu Lys Leu Tyr Lys Leu
1               5                   10                  15

Lys Glu Thr Trp Trp Glu Thr Trp Trp Thr Glu Trp Ser Gln Pro Lys
            20                  25                  30

Lys Lys Arg Lys Val
        35

<210> SEQ ID NO 30
<211> LENGTH: 37
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: FITC

<400> SEQUENCE: 30

Arg Trp Glu Lys Ile Ser Ile Ile Asn Phe Glu Lys Leu Tyr Lys Leu
1               5                   10                  15

Ala Gly Tyr Leu Leu Gly Lys Ile Asn Leu Lys Ala Leu Ala Ala Leu

Ala Lys Lys Ile Leu
        35

<210> SEQ ID NO 31
<211> LENGTH: 37
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (37)..(37)
<223> OTHER INFORMATION: FITC

<400> SEQUENCE: 31

Gly Leu Trp Arg Ala Leu Trp Arg Leu Leu Arg Ser Leu Trp Arg Leu
1               5                   10                  15

Leu Trp Arg Ala Arg Trp Glu Lys Ile Ser Ile Ile Asn Phe Glu Lys
            20                  25                  30

Leu Tyr Lys Leu Lys
        35

<210> SEQ ID NO 32
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: FITC
<220> FEATURE:
<221> NAME/KEY: MOD_RES
<222> LOCATION: (25)..(25)
<223> OTHER INFORMATION: Cholesterol

<400> SEQUENCE: 32

Leu Glu Gln Leu Glu Ser Ile Ile Asn Phe Glu Lys Leu Thr Glu Trp
1               5                   10                  15

Arg Val Arg Arg Ala Leu Ile Ser Cys
            20                  25

<210> SEQ ID NO 33
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Cholesterol
<220> FEATURE:
<221> NAME/KEY: MOD_RES
<222> LOCATION: (25)..(25)
<223> OTHER INFORMATION: FITC

<400> SEQUENCE: 33

Cys Arg Val Arg Arg Ala Leu Ile Ser Leu Glu Gln Leu Glu Ser Ile
1               5                   10                  15

Ile Asn Phe Glu Lys Leu Thr Glu Trp
            20                  25